United States Patent
Baruch

(10) Patent No.: US 11,207,034 B2
(45) Date of Patent: Dec. 28, 2021

(54) SELF-CALIBRATING SYSTEMS AND METHODS FOR BLOOD PRESSURE WAVE FORM ANALYSIS AND DIAGNOSTIC SUPPORT

(71) Applicant: CareTaker Medical, LLC, Charlottesville, VA (US)

(72) Inventor: Martin Baruch, Charlottesville, VA (US)

(73) Assignee: CareTaker Medical, LLC, Charlottesville, VA (US)

( * ) Notice: Subject to any disclaimer, the term of this patent is extended or adjusted under 35 U.S.C. 154(b) by 516 days.

(21) Appl. No.: 16/029,230

(22) Filed: Jul. 6, 2018

(65) Prior Publication Data

US 2019/0059825 A1 Feb. 28, 2019

Related U.S. Application Data

(60) Provisional application No. 62/529,196, filed on Jul. 6, 2017.

(51) Int. Cl.
  *A61B 5/00* (2006.01)
  *A61B 5/022* (2006.01)
  *A61B 5/0225* (2006.01)
  *A61B 5/021* (2006.01)

(52) U.S. Cl.
  CPC .......... *A61B 5/7278* (2013.01); *A61B 5/0225* (2013.01); *A61B 5/02116* (2013.01); *A61B 5/02225* (2013.01); *A61B 5/02241* (2013.01); *A61B 5/7221* (2013.01); *A61B 5/742* (2013.01); *A61B 2560/0228* (2013.01); *A61B 2562/0247* (2013.01)

(58) Field of Classification Search
  CPC .............. A61B 5/7278; A61B 5/02116; A61B 5/02225; A61B 5/02241; A61B 5/0225; A61B 5/7221; A61B 5/742; A61B 2560/0228; A61B 2562/0247
  USPC ........................................................ 600/494
  See application file for complete search history.

(56) References Cited

U.S. PATENT DOCUMENTS

| | | |
|---|---|---|
| 4,846,189 A | 6/1989 | Sun |
| 6,491,647 B1 | 12/2002 | Bridger et al. |
| 6,723,054 B1 | 4/2004 | Baruch |
| 7,087,025 B2 | 8/2006 | Baruch |

(Continued)

FOREIGN PATENT DOCUMENTS

| | | |
|---|---|---|
| CN | 1771005 A | 5/2006 |
| CN | 106344042 A | 1/2017 |

OTHER PUBLICATIONS

International Search Report and Written Opinion dated Oct. 25, 2018, for International Application No. PCT/US2018/041093, 8 pages.

(Continued)

*Primary Examiner* — David J. McCrosky
*Assistant Examiner* — Chanel J Jhin

(57) ABSTRACT

Indirect, oscillometric, digital blood pressure monitoring systems and methods enabling self-calibration to obtain absolute blood pressure values using algorithmic analysis of arterial pressure pulses to establish an oscillometric profile and compensate for intervening effects on digital arterial pressure. Proper algorithmic analysis is dependent upon proper positioning and maintained engagement of a digital cuff on the digit of a user and subsequent hydraulic coupling of the cuff to the arteries within the digit.

14 Claims, 16 Drawing Sheets

(56) References Cited

U.S. PATENT DOCUMENTS

| | | |
|---|---|---|
| 8,100,835 B2 | 1/2012 | Baruch |
| 2006/0253041 A1 | 11/2006 | Shin et al. |
| 2007/0287923 A1 | 12/2007 | Adkins et al. |
| 2009/0318779 A1 | 12/2009 | Tran |
| 2010/0222655 A1 | 9/2010 | Starr et al. |
| 2010/0262022 A1 | 10/2010 | Baruch et al. |
| 2012/0238887 A1 | 9/2012 | Gerdt et al. |
| 2012/0330109 A1 | 12/2012 | Tran |
| 2015/0148694 A1 | 5/2015 | Baruch |
| 2015/0186609 A1 | 7/2015 | Utter, II |
| 2016/0045119 A1 | 2/2016 | Gerdt et al. |
| 2016/0120420 A1 | 5/2016 | Liedl |
| 2019/0029542 A1 | 1/2019 | Li et al. |
| 2019/0104953 A1 | 4/2019 | Narasimhan |
| 2019/0167128 A1 | 6/2019 | Baruch |

OTHER PUBLICATIONS

International Search Report and Written Opinion dated Apr. 18, 2019, for International Application No. PCT/US2018/063890, 8 pages.

Nesselroad, JM: Flacco, VA; Phillips, DM; Kruse, J; Accuracy of Automated Finger Blood Pressure Devices, Family Medicine Mar. 1996; pp. 28(3):189-92.

Veerman DP; Lenders, JW; Thein T; Van Montfrans, GA; LAM 100/Marshall F-88: Accuracy and Precision of a New Device for Discontinuous Finger Blood Pressure Measurement; Journal of Human Hypertension, Apr. 1993; 7(2):113-5.

Lyew, MA; Jamieson, JW; Blood Pressure Measurement Using Oscillometric Finger Cuffs in Children and Young Adults. A Comparison with Arm Cuffs During General Anesthesia; Anesthesia; Oct. 1994; 49(10):895-9.

Lee, JY; Kim, JK; Yoon, G; Digital Envelope Detector for Blood Pressure Measurement Using an Oscillometric Method; Journal Medical Engineering & Technology; May-Jun. 2002(3): 117-22.

Babbs, CF: Oscillometric Measurement of Systolic and Diastolic Blood Pressures Validated in a Physiological Mathematical Model; Biomed Engineering Online; Aug. 22, 2012; 11:56; https://doi.org/10.1186/1475-925X-11-56.

Gizdulich, P; Prentza, A; Wesseling, KH; Models of Brachial to Finger Pulse Wave Distortion and Pressure Decrement; Cardiovascular Research; Mar. 1997; 33(3);698-705.

Advancing Safety in Medical Technology; Non-invasive sphygmomanometers—Part 2: Clinical investigation of automated measurement type; ANSI/AAMI/ISO 81060-2:2013.

Extended European Search Report dated Apr. 8, 2021, for European Application No. 18828614.0, 13 pages.

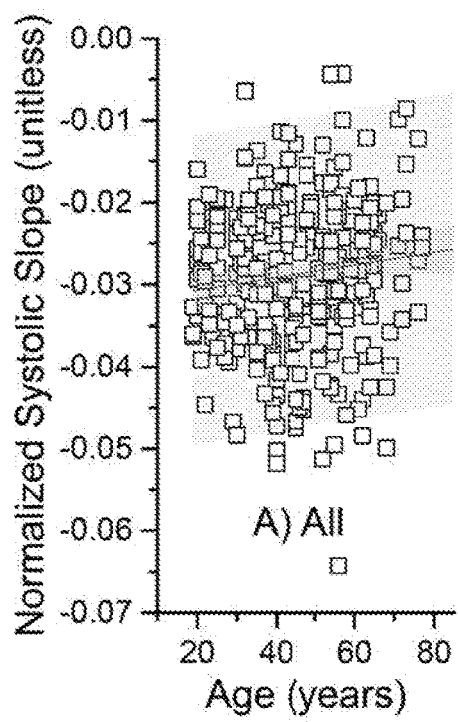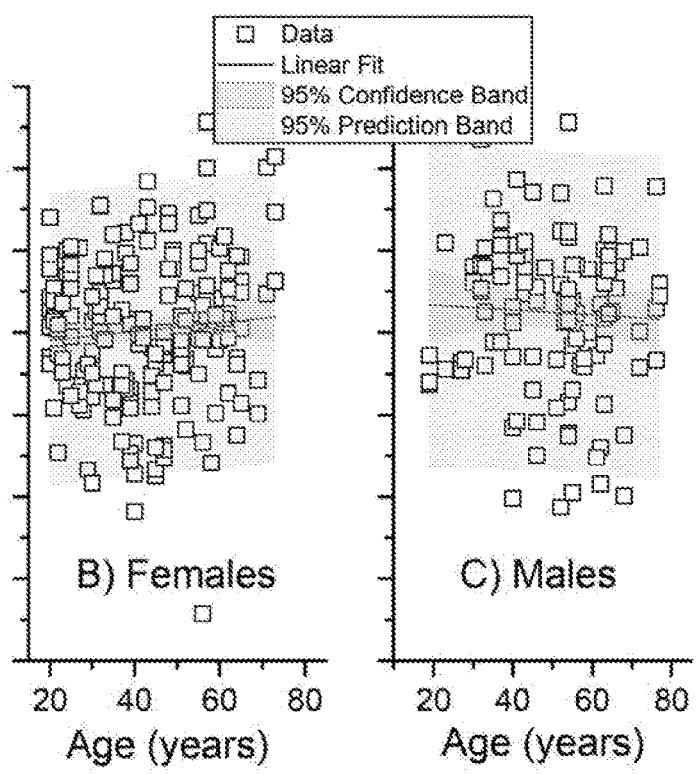
Figure 8A  Figure 8B  Figure 8C

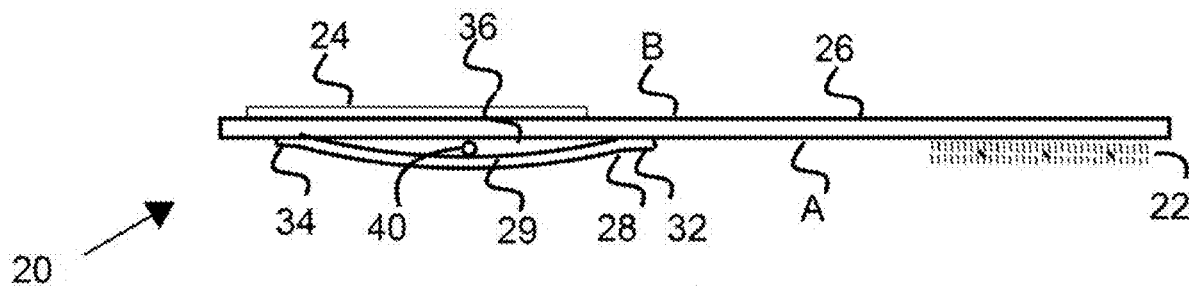
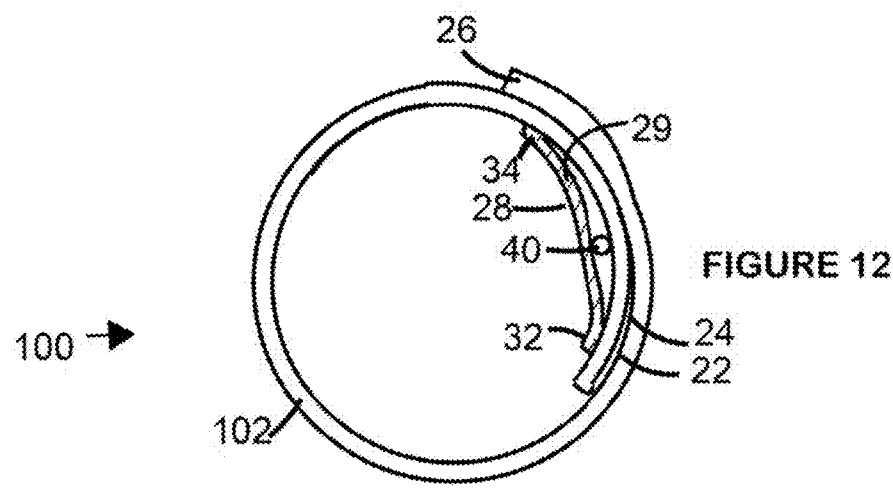

SELF-CALIBRATING SYSTEMS AND METHODS FOR BLOOD PRESSURE WAVE FORM ANALYSIS AND DIAGNOSTIC SUPPORT

CROSS-REFERENCE TO RELATED APPLICATIONS

This application claims priority to and the benefits of U.S. Provisional Applicaton No. 62/529,196, filed Jul. 6, 2017, the disclosure of which is hereby incorporated by reference herein in its entirety.

This application hereby incorporates, in their entireties, by reference thereto: U.S. patent application Ser. No. 13/231,703 filed Sep. 13, 2011; US Patent Application Publication No. 2012/0238887; U.S. patent application Ser. No. 12/854,954 filed Aug. 12, 2010, U.S. application Ser. No. 12/537,228 filed Aug. 6, 2009; U.S. application Ser. No. 11/500,558 filed Aug. 8, 2006; U.S. Pat. No. 7,087,025; U.S. application Ser. No. 11/803,643 filed May 15, 2007; U.S. Pat. Nos. 6,723,054; 8,001,835 and U.S. Provisional Application Ser. No. 61/946,277 filed Feb. 28, 2014.

FIELD OF THE INVENTION

The present invention relates to the self-calibration of blood pressure tracking systems infer blood pressure by indirect means, such as, for example, through time-delay measurements of the arterial pressure pulse or using pulse waveform analysis in general.

BACKGROUND OF THE INVENTION

There have been many attempts to deduce arterial blood pressure from arterial sites other than the traditionally used brachial artery site of the upper arm. The motivation is related to comfort and fit issues, as well as to the increasing awareness that continuously measured blood pressure is superior to occasional point-in-time measurements. The comfort and fit issues associated with traditional upper arm cuffs makes them a less attractive technology candidate, particularly when monitoring awake or sleeping patients, as opposed to anesthetized patients. Finger cuff-based blood pressure measurements are far better tolerated in these particular populations. This motivation has fueled the development of two broad classes of non-invasive continuous blood pressure monitoring technologies: 1) those that are non-invasive but intrusive, and 2) those that aim to be both non-invasive and non-intrusive.

Penaz-principle based devices and tonometers, while non-invasive, are intrusive due to their aggressive coupling to the monitored artery as well as the footprint and power requirements due to the nature of their underlying technology.

Blood pressure tracking systems that are both non-invasive but also non-intrusive (NINI) utilize, for example, the relationships between arterial pressure and pulse propagation velocity, i.e. pulse transit time (PTT), or pulse waveform analysis (PWA) to infer blood pressure continuously or beat-to-beat. These NINI systems currently frequently utilize one of the digits to obtain at least part of the physiological signals required for their operation.

The finger as an arterial pulse monitoring site has significant advantages. Its approximately cylindrical shape facilitates the stable coupling and, equally important, reproducible application of a sensor to the arterial pulsations through removal and re-application cycles. Digital arterial monitoring sites, in contrast to the radial artery site of the wrist, for example, are not subject to rotations or twists and the associated skin stretches and displacements. The digits of high BMI (body mass index) patients tend not to exhibit the same excess tissue that characterizes major limbs, High pressure application to the digits, if confined to time scales of a minute or so, is well tolerated, particularly by the geriatric population that tends to exhibit the least tolerance for upper arm cuff inflations. The time scale consideration mentioned is very important, because the intolerance of patient populations to the long term application of high pressure to digits, such as utilized by Penaz principle-based systems, is well documented.

While there are a number of issues associated with the digits as an arterial pulse monitoring site that will be discussed in more detail below, a well-known disadvantage is that, as part of the distal arterial periphery, the digital arteries are subject to throttling mechanisms, such as due to temperature, that can affect perfusion significantly. In addition, while the brachial site of the upper arm is usually adjacent to the heart, requiring no hydrostatic head compensation, this is usually not the case unless hand/heart positions are specified or the patient is supine/prone.

Since PTT or PWA blood pressure monitoring systems, and in particular blood pressure monitoring systems utilizing PDA, infer blood pressure indirectly, they require initial and/or recurring calibrations with a direct blood pressure measurement. Frequently these systems use an externally obtained blood pressure, for example a blood pressure obtained from an upper arm cuff. This is not optimal as it requires more hardware to be included in the monitoring system, the interfacing of the additional component, and the mentioned patient comfort issue. Due to the significant sizing requirements of upper arm cuffs, it also involves inclusion of different adult-size upper a cuffs, even more if a thigh cuff is to be included, in the monitoring system.

Using a digit itself as a site for the self-calibration measurement of, an absolute blood pressure would therefore be clearly preferred, particularly if the self-calibration procedure could utilize the digital sensing enclosure that is already being used for continuous blood pressure tracking.

Despite decades of research there are still today no non-invasive blood pressure calibration methods available that do not involve the direct application of a known pressure to an artery to determine the pressure within it. The difficulty in determining such a method lies in that all indirect, surrogate measures of arterial pressure, for example pulse transit time, pulse shape changes etc. are subject to physiological confounders, such as vasodilation or constriction, that can produce the identical surrogate measure at significantly different blood pressures.

Traditionally, direct blood pressure measurements subject the artery to a sequence of external pressures that modulate blood flow, ranging step-wise in pressure from complete obstruction to complete release while the arterial wall response during the traversing blood pressure pulse is measured. Traditional arm cuff measurement cycles typically start with the external pressure initially high enough that the artery collapses and blood flow ceases. The external pressure is then gradually released, whether in steps or continuously. With dropping external pressure the blood will initially spurt through the obstructed arterial region, the onset of which corresponds approximately to systole. Further reduction of the external pressure will allow the artery to expand further while unloading its wall stress, which in turn allows the wall to oscillate with greater amplitude with each heartbeat than it would in its natural, loaded wall tension state. At approximately mean arterial pressure the wall stress unloading is optimal, producing the largest oscillatory signal. With further dropping external pressure the wall unloading diminishes until the wall stress is restored, blood flow is unimpeded, and the oscillations cease. The pressure at which flow resumes unimpeded corresponds approximately to diastolic pressure. When auscultatory methods are used, whether involving devices or clinicians, these pressure points are determined by listening for the characteristic blood flow turbulence sounds, i.e. Korotkoff sounds, of each flow stage.

Automated oscillometric measurement approaches analyze the shape of the oscillometric "hill", the response curve that plots oscillometric amplitude versus external pressure, utilizing statistical averages of invasive blood pressure and oscillometric measurement comparisons across different patient populations to establish generally valid thresholds. In the case of upper arm oscillometric cuffs a generally accepted threshold for systole is 50% of full amplitude on the high pressure side for systole, and 70% on the low pressure side for diastole. In practice, the analysis algorithms used by monitor manufacturers are all proprietary.

While the concept of oscillometry involving upper arm cuffs is well established, the use of oscillometry to obtain blood pressure readings from the digits is less well known and to date has not succeeded acceptably. Specifically, no prior art approaches using oscillometry on the finger have been able to meet the specifications set for FDA-cleared blood pressure monitors, the most recent version being the ANSI/AAMI/ISO 81060-2:2013 standard. The core of the standard are two conditions: 1) the bias of paired readings obtained from the monitor under test against the Gold Standard has to be within 5 mmHg and their standard deviation has to be within 8 mmHg: and 2) the bias and standard deviation are related via a specified formula, the net effect being that, as the bias increases, the standard deviation limit shrinks. As an example, if the bias of the paired readings is 4.3 mmHg, the standard deviation can be no larger than 5.41 mmHg. Other central requirements are the distribution of blood pressures to be measured and the number of subjects/readings.

A number of investigators have examined the feasibility of the use of oscillometry to obtain blood pressure readings from the digits as part of development and clinical comparison studies, with results ranging from poor. [1]with no statistically significant correlation with a clinical Gold Standard being found, to reasonable, [2]where a commercially available device, the Marshall F-88, matched the performance of the FDA-approved Finapres device but both performed outside 81060 guidelines. Likewise, the results of a study by Lyew[3] that compared the performance of standard arm readings with those from forefinger cuffs in a cohort of 41 children and young adults met the bias requirements of the guidelines and came within less than 2 mmHg of the standard deviation requirements on both systole and diastole. A group at Samsung that has been developing related technology more recently claimed performance well within the guidelines. [4] However, the lack of any follow-up makes these claims questionable.

This lack of success is notable, considering that some Penaz principle-based devices that use the Physiocal self-calibration approach, which also involves the pressure step-wise interrogation of the arterial pulsatile response, have met the 81060 standard in comparisons against invasive arterial catheters, considered the Gold Standard of blood pressure comparisons. Other Penaz principle devices use upper arm cuffs to provide calibration, i.e. they do not self-calibrate in the sense described here, using the same finger cuff that is used for continuous monitoring for the calibration sequence.

The reason why Peñáz/Phystiocal devices have succeeded reasonably, while oscillometric measurements on the finger have fallen short, is likely two-fold. On the one hand is the fact that as part of the development of the volume clamp method the changes the arterial pressure pulse undergoes when it reaches the finger have been much more carefully studied and modeled. Secondly, the Physiocal method has available the input of two sensing systems. One being the electric current requirements of the pump motor and the corresponding pressure generated. The other is the optical response signal, which provides feedback on how the pump-driven pressure modulations are affecting the arterial pulse response and blood volume.

Oscillometric approaches, one the other hand, usually only employ a single bladder-artery interface that is used to both engage the artery through pressure increases and to sense the arterial pulse response. Considering ease of use and economics, a single finger cuff is clearly preferred over the cumbersome current blood pressure monitoring technology.

Previous attempts to use a digital cuff for obtaining a self-calibration measurement of an absolute blood pressure have failed because simple assumptions were made about how brachial and digital blood pressures are related, the primary previous concern having been that the gravitational difference between the two points, the hydrostatic head, has to be compensated for by keeping the monitored hand at heart height.

As discussed herein, the issues affecting a blood pressure calibration system operating on the finger establish the lever of sophistication and non-trivialness required for the task. This is despite the fact that the use of oscillometry on the finger would appear to be an extension of an established methodology. Use of oscillometry on the finger requires overcoming a host of issues that are not encountered when using oscillometry on the arm. While arterial finger cuff blood pressure monitoring is very desirable as set forth above, a non-invasive blood pressure calibration method for such arterial blood pressure monitoring systems is needed to enhance patient comfort, increase monitoring efficiency, and improve patient care. While some theoretical physiological modeling is possible, the best approach appears to be, given the enormous range of human digital physiologies, to create oscillometric response analysis models on the basis of sufficiently large human populations.

In order to develop the self-calibration blood pressure monitoring capability proposed by the present invention, the physiological effects that affect blood pressure on the finger must be identified and considered.

SUMMARY OF THE INVENTION

In accordance with the present invention an indirect blood pressure monitoring system enabling self-calibration to obtain absolute blood pressure values is provided which includes a digital cuff having an air bladder and a securing mechanism; a receiving module, having electronic components, in communication with the digital cuff; an air conduit in pneumatic communication with the digital cuff and the receiving module; a pressure controlling means within the receiving module; a processor connected to the receiving module; and a display mechanism.

The securing mechanism maintains engagement between the cuff and the digit on which the cuff is positioned while the air bladder is pressurized through the air conduit by the pressure controlling means to a pressure less than said user's diastolic blood pressure, thereby circumferentially squeezing the digit to partially unload artery and creating a hydraulic coupling between the at least one artery within the digit and the air bladder. The hydraulically coupled air bladder detects pulse pressure oscillations caused by pulse pressure waves passing through the coupled artery, and the pressure oscillations are sensed by at least one pressure sensor of the pressure controlling means, which is transmitted to the processor for analysis. The pressure controlling means is controlled by the receiving module. The operation of the digital cuff is also controlled by the receiving module to take either absolute or relative blood pressure readings.

The processor is configured to run an algorithm analyzing real-time pressure change data received from the digital cuff when taking absolute blood pressure readings in relation to filed pressure change clinical data. The algorithm extracts parameters affecting digital pulse pressure, establishes an oscillometric profile as a function of pressure, and considers intervening effects on digital pulse pressure. The processor uses the oscillometric profile to derive a calibrated, absolute blood pressure value against which a relatively continuous blood pressure monitoring mode will track changes in blood pressure. The calibrated, absolute blood pressure value matches within guidelines set by ANSI/AAMI/ISO 81060-2:2013 standard.

The intervening effects affecting pulse pressure include coupling of blood pressure monitoring device, number of arteries being monitored, arterial stiffness, tissue variations, filtering effects, pressure pulse amplification and spectral content of arterial pulse.

In accordance with the present invention, the processor analyzes real-time pressure change data using a method of calibration including:

i) detecting arterial pulse peak of the arterial pulse from oscillometric pressure scans;

ii) deriving the oscillometric profile as a function of pressure from said arterial pulse peak, the oscillometric profile having a diastolic side, a systolic side, a slope, and an amplitude;

iii) testing the oscillometric profile for irregularities due to cuff positioning or scan errors;

iv) rejecting or accepting the oscillometric profile based on presence or absence of irregularities;

v) determining preliminary threshold values for systole and diastole, the preferred values being 70% of the maximum amplitude of the oscillometric profile for systole and 50% of the maximum amplitude of the oscillometric profile for diastole;

vi) categorizing the profile into low, normal, or high blood pressure ranges based on the preliminary systole and diastole values;

vii) adding an offset for systole based on the categorization;

viii) estimating tissue coupling by assessing said amplitude and systolic slope of the oscillometric profile in the low pressure range to calculate an offset to be subtracted from ultimate blood pressure values based on pressure required to penetrate intervening tissue to engage the arteries;

ix) assessing the spectral content of the arterial pulse at different pressure steps of an oscillometric scan;

x) assessing sides of the diastolic slope and systolic slope of the oscillometric profile:

xi) calculating the final systolic and diastolic thresholds; and xii) applying offsets to said final thresholds.

In accordance with the present invention, the cuff is placed in a position a finger that substantially conforms to the shape of the finger thereby eliminating gaps between the finger and cuff and equally engaging both of the two arteries in the finger.

In accordance with the present invention, the air bladder of the digital cuff is uniformly supported by a semi-cylindrical enclosure sufficiently rigid to pressure-contain the air bladder to provide for hydraulic coupling of the air bladder with the at least one artery, so that 1) increases in inflation pressure of the air bladder of the digital cuff from the receiving module are directed to the at least one digital artery by the hydraulic coupling and 2) pressure oscillations induced in the cuff by arterial pressure waves are contained within said air bladder and directed to the air conduit.

BRIEF DESCRIPTION OF THE DRAWINGS

FIG. 8A-C shows the age dependence of the normalized systolic slope of the oscillometric profile for FIG. 8A) the entire cohort, FIG. 8B) females only, FIG. 8C) males only according to an embodiment of the present invention.

FIG. 11 is an example digital cuff according to an embodiment of the present invention, FIG. 12 is the example digital cuff of FIG. 11 in the closed position according to an embodiment of the present invention.

DEFINITIONS

Figures 1A, 1B, 1C:
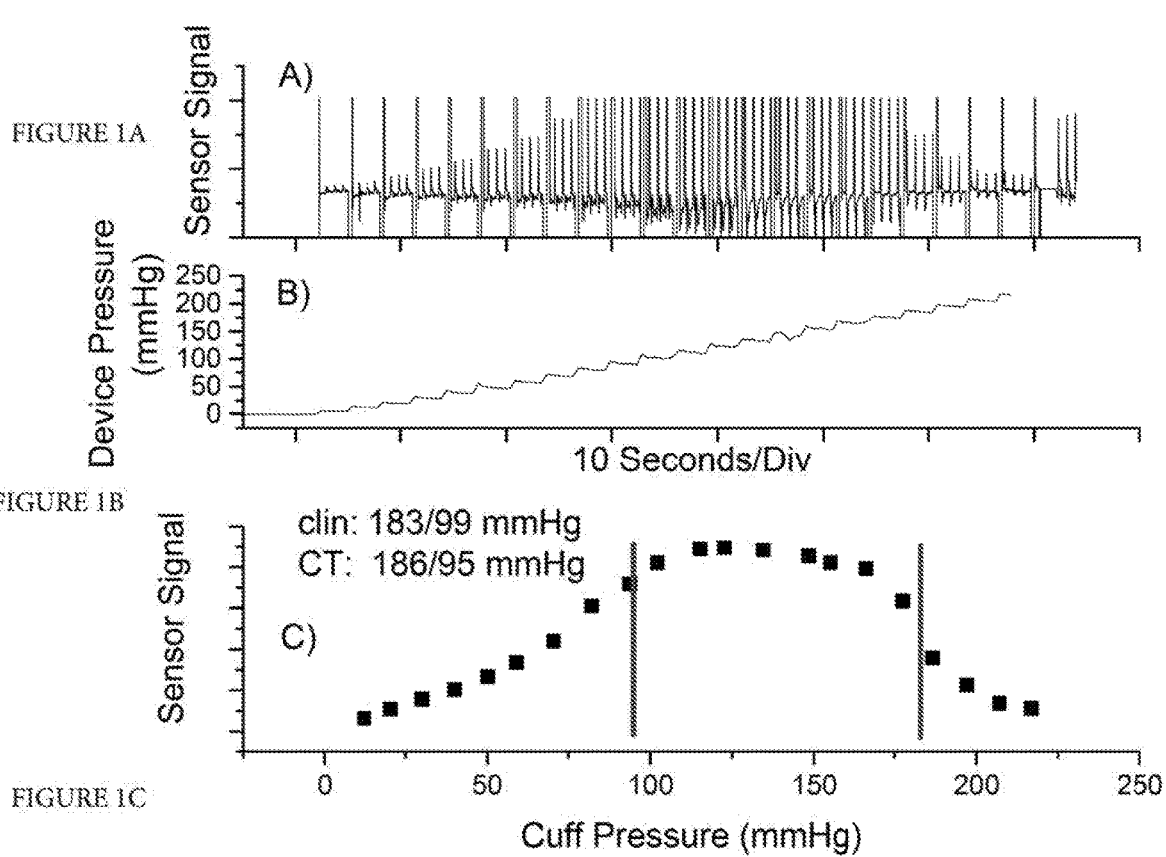
FIG. 1A illustrates sensor signal for the acquisition of signal during a pressure scan according to an embodiment of the present invention.
FIG. 1B illustrates device for the acquisition of signal during a pressure scan according to an embodiment of the present invention.
FIG. 1C the resulting oscillometric profile from FIG. 1A and FIG. 1B according to an embodiment of the present invention.

As used herein the term "about" refers to a variation of +/−15%.

As used herein the term "auscultatory method" shall refer to determining blood pressure through the use of a stethoscope and a manometer. The auscultatory method is the predominant method of clinical measurement.

As used herein "absolute blood pressure" shall refer to systolic and diastolic pressures obtained via direct pressure measurements, such as via an invasive arterial catheter or non-invasive means that couple directly to the arterial pulse pressure.

As used herein "relative blood pressure" shall refer to systolic and diastolic pressures obtained by measuring changes in blood pressure.

As used herein the term "oscillometric" shall refer to the measurement of oscillations, which in the context here are arterial wall oscillations due to the passing arterial pressure pulse and accentuated by the wall's stress unloading due to the supporting finger cuff.

As used herein the term "digital cuff" shall refer to a suitable semi-cylindrical enclosure that enables a slightly pressurized air bladder to couple to the digital arteries and allows said bladder to relieve the received arterial pressure modulations only via a connected pneumatic hose.

As used herein "computing device" shall refer to any device having computing capability, communication means and storage, including but not limited to PC, Mac, tablet, smart phones, watches, etc.

As used herein the term "HRV" shall refer to heart rate variability, the physiological phenomenon of variation in the time interval between heartbeats. It is measured by the variation in the beat-to-beat interval.

As used herein "PDA" shall refer to Pulse Decomposition Analysis. For a full disclosure of PDA technology see U.S. Pat. No. 7,087,025. Blood Pressure Determination Based on Delay Times between Points on a Heartbeat Pulse, pending patent application, Ser. No. 12/537,228, Detection of Progressive Central Hypovolemia, filed 6 Aug. 2009, pending patent: Ser. No. 11/500,558, Method for Arterial Pulse Decomposition Analysis for vital Signs Determination, and Diagnostic Support Apparatus, PCT/US10/43914, filed 30 Jul. 2010, which are incorporated herein by reference, as though recited in full.

As used herein "receiving module" shall refer to any device receiving data from the finger cuff capable of having a computing capability, communication means, and storage, As used herein the term "T01" shall mean the rise time of the P1 pulse, or the front end of the composite pulse As used herein the term "T13" shall mean the calculated interval between the systolic and iliac peaks.

As used herein the term "P1" shall refer to the original systolic pulse peak.

As used herein the term "P2" shall refer to the renal reflection pulse.

As used herein the term "P3" shall refer to the iliac peak.

As used herein the term "external calibration" shall refer to the calibration of the continuous blood pressure monitoring technology using a device/technology external to/separate from the continuous blood pressure monitoring technology, for example an upper arm cuff.

As used herein the term "self-calibration" shall refer to the calibration of the continuous blood pressure monitoring technology using a device/technology that is part of the normal continuous blood pressure monitoring operation, for example the finger cuff that is also used for continuous operation.

As used herein the term "calibration" shall refer to the calibration of the continuous blood pressure monitoring technology in general, i.e. providing the continuous blood pressure monitoring technology a starting point, in terms of absolute blood pressure values, from which to track relative changes in blood pressure from.

DETAILED DESCRIPTION OF THE INVENTION

Before the present systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

The present invention incorporates the continuous blood pressure tracking technology Pulse Decomposition Analysis (PDA) as disclosed in U.S. Pat. Nos. 8,100,835 and 7,087,025. The disclosed system enables self-calibration, without the addition of new hardware components, to obtain absolute blood pressure values to calibrate the relative blood pressure values obtained during tracking. Furthermore, these absolute blood pressure values match, within guidelines set for example by the ANSI/AAMI/ISO 81060-2:2013 standard, those obtained during standard-of-care measurements, which currently are obtained from upper arm cuffs or arterial catheters. In particular, the invention relates to self-calibration at arterial sites other than the commonly used brachial artery of the upper arm, such as, for example, the digits.

Finger cuff-based blood pressure measurements are far better tolerated and critical in certain patient populations. In high BMI patients it can be almost impossible to obtain a reliable, non-invasive BP because no cuff size fits them. Women whose lymph nodes have been removed as part of mastectomies cannot tolerate upper arm cuffs, making it that only leg cuffs can be used on double-mastectomy patients. The frail elderly do not tolerate upper arm cuff inflations well.

As noted herein, previous attempts to use digital cuffs to obtain a self-calibration measurement of an absolute blood pressure have failed due to insufficient research leading to incorrect assumptions about how brachial and digital blood pressures are related. Previously the primary concern was that the gravitational height difference between the heart and monitored hand, referred to as the hydrostatic head, had to be compensated for by keeping the monitored hand at heart height.

The disclosed method succeeds because it is based on a comprehensive approach that incorporates the various intervening physiological effects on digital blood pressures that previous approaches did not take into account. Obtaining such a comprehensive picture of the intervening effects was achieved due to the significant physiological model-building during the development of the FDA formalism, which in turn was based on extensive literature searches as well as the development and validation testing of original concepts regarding the structure of the arterial pulse and the changes it undergoes during its propagation from the heart to the periphery. Extensive data were collected to map out the, at times unexpected, differences between digital and brachial blood pressures and to compensate for these effects in the analyzing algorithm.

One of the intervening effects on digital and brachial blood pressures is arterial stiffness. Effects of variations in arterial stiffness on the shape and threshold shifts of the oscillometric pressure hill were examined by Babbs[5] in a physiological mathematical model. The study examined the physiology of the brachial artery as it would affect an upper arm cuff. Similar considerations apply to the digital arteries. The central point of the study is that increasing arterial stiffness changes both slopes of the oscillometric hill, necessitating changes in the height thresholds commonly assigned for the determination of diastole.

Babb's previously mentioned oscillometric model is a useful place to start in gaining a preliminary understanding of the effects of arterial stiffness on the shape of the oscillometric hill and therefore the thresholds. Even just considering the effects of arterial stiffness, the understanding gained will be preliminary due to the fact that the presentation of the model is purely theoretical, i.e. with no comparisons to any clinical data, and it considers only specifications applicable to the brachial artery.

Figure 2:
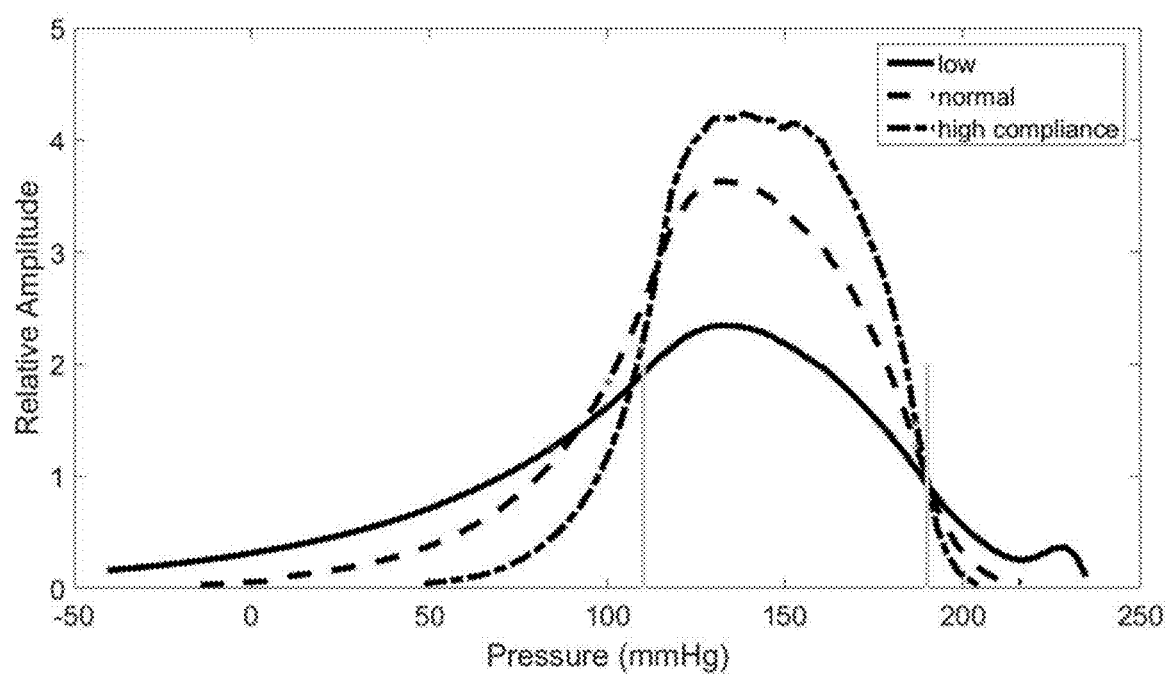
FIG. 2 shows a simulation of oscillometric pressure sweeps for different relative arterial stiffnesses according to an embodiment of the present invention.

FIG. 2 displays an example of the results that Babb's model provides. The bottom figure displays the results of simulations of oscillometric pressure sweeps, for different relative arterial stiffnesses. The slopes of the oscillometric hill profile flatten as arterial stiffness is increased, or arterial compliance decreases. As a result threshold markers, which are established as a percentage of maximum height and that are used to determine diastole and systole, shift. The effect is, according to the model, particularly pronounced on the diastolic side. The vertical gray bars indicate the systolic and diastolic blood pressures input into the model. The graph of FIG. 2B displays the derivatives of the FIG. 2A graph plots.

One prediction of the above model is that, as arterial compliance increases, both systolic and diastolic characteristic thresholds change. Specifically, for this specific case examining a high blood pressure case of 190/110, the diastolic threshold decreases from 82% of full maximum for a low-compliance artery to 73% to 60.5% for, respectively, doubled and doubled again compliance, while the corresponding down-shift in systole is 31%, 19% and 12.3%. Based on the model's predictions the thresholds also shift with blood pressure levels, an effect that is pronounced for systole as the pressure approaches and exceeds 200 mmHg, particularly as pulse pressure approaches and exceeds 100 mmHg. While the Babbs model of FIG. 2 is useful for the examination of some aspects, in light of the many previously listed physiological factors that play a role in shaping the blood pressure response on the finger, the emphasis has been on examining trends in the clinical data itself.

Tissue and arterial stiffness variations, whether intra or inter-subjects, are a major concern and intervening effect. The tissue consideration is related to the fact that the digital arteries are not palpable, i.e. layers of intervening tissue mask the arterial pulsations and, while different subjects will feature different tissue thicknesses depending on lifestyle and genetics, the elasticity of these layers will change for the same subject depending the state of perfusion, hydration, temperature etc. Since the arteries themselves feature a smooth muscle wall layer, the wall response will change depending on the state of arterial wall stiffness. This has major implications for a pressure-dependent approach that seeks to interrogate the artery's elastic/pressure response. If substantial layers of tissue have to be "pressed through" to engage the artery, the onset of the pulsatile arterial pressure pulse, i.e. diastole, as well as the entire oscillometric pressure hill will be delayed to a higher pressure. If this offset is not compensated for, the actual blood pressure readings will be increased by this offset. In addition the slopes of the oscillometric pressure hill will change depending on whether the arterial wall and the intervening tissue respond more or less elastically to the pressure-dependent interrogation by the pressurized bladder of the finger cuff.

Another intervening effect with similar considerations as arterial stiffness is poor coupling of a blood pressure monitoring device, such as is the case with cold fingers. Due to decreased perfusion the arterial pulse signal is depressed and the surrounding tissue is less pliable, which dampens the slope response of the oscillometric signal. In addition, examination of the arterial pressure pulse shape makes it possible in principle to distinguish coupling-related arterial stiffness issues.

Another intervening effect is that the flow resistance of the smaller digital arteries lowers the arterial pressure, particularly as it applies to diastole and mean arterial pressure.

The intervening effects of pressure pulse amplification and mechanical filtering enhance the systolic part of the arterial pressure pulse. Pulse amplification is due to the changing composition of the arterial wall and the taper of the arterial diameter as the pressure pulse propagates toward the arterial periphery, compressing it temporally which in turn raises its amplitude. This potentially also increases the variability of the systolic side of the oscillometric hill due to the blood pressure modulations associated with respiration, which are likely to be enhanced by the pulse amplification effects.

Frequency-dependent filtering effects also affect digital blood pressure. In regard to frequency-dependent filtering effects, Gizdulich[6] examined the relationship between brachial and digital pulse shapes in detail, finding that, while low frequencies in the pressure pulse profile are attenuated, frequencies around 7 Hz are amplified. This effect is clearly different from the mechanical filtering effect that was mentioned earlier, which would be expected to have low-pass effects, i.e. enhancing low-frequency components while attenuating high frequency components. This again could contribute to increased variability that has been observed by several authors with increasing systolic pressure since higher pressure pulses typically are associated with stiffer arterial systems, which mechanically low-pass filter the pressure pulse.

[6] Gizdulich P, Prentza A, Wesseling K H., Models of brachial to finger pulse wave distortion and pressure decrement, Cardiovasc Res. 1997 March; 33(3):698-705.

Another factor driving the frequency dependence is the differential response of the reflection components of the pressure pulse envelope to oscillometric pressure sweep. Put differently, the reflection component pulses P2 and P3 respond earlier to the pressure sweep than P1, the direct left ventricular ejection pulse, because of their comparative smaller amplitudes. The resulting effect of the progressing oscillometric pressure is therefore not just the amplitude decrement of the arterial pressure pulse, but a significant change in its shape, which in turn changes its frequency content.

Another issue that is unique to blood pressure calibration on the finger is the fact that two arteries are being interrogated, not one as in the upper arm brachial artery case. This, as well as the conical/cynlindrical geometry of the digits, places additional requirements on the finger cuff and how it assures equal coupling of the inflating bladder against both arteries. Due to the finger shape and the presence of two arteries, the finger cuff must fit the finger so that there are no gaps between the finger and the bladder. If there are gaps, the bladder will expand into those voids in unpredictable ways, distorting the oscillometric hill that is analyzed to obtain calibrated starting blood pressures. If the cuff does not provide uniform support to the inflating bladder, the bladder will tend to engage one artery first, and then, eventually, the other, leading to a severely distorted, typically two-horned, oscillometric hill that will provide very inaccurate readings. On the signal processing side, care has to be taken to identify when the loading is unequal and what the response of the processing algorithm to the identification of this condition will be. The algorithm is self-standing and assesses whether the cuff was placed correctly based on the shape of the oscillometric hill.

A consideration specific to the disclosed system is that the detection of the derivative arterial pressure pulse signal will amplify the frequency-related effects. As the pulse shape is modified and compressed in time during the oscillometric scan, its frequency content up-shifts, which, because of the nature of derivatives, would translate into an amplitude increase that "prolongs" the systolic side descent of the oscillometric hill profile.

In what follows, the general approach to implementing compensatory means for the intervening effects described above is outlined, concluding with the description of a formalism that provides for the quantitative determination of systolic and diastolic blood pressure values.

In order to obtain a starting calibration or a re-calibration for a continuous blood pressure monitoring system, such as the PDA technology implemented on the Caretaker (CT) finger cuff blood pressure monitor, the first step is to perform a blood pressure sweep with the digital cuff monitoring system. These pressure sweeps collect data that is processed by the system's algorithm that is implemented to compensate for the intervening effects of digital blood pressure. The clinical data collected by the disclosed system during a given blood pressure recording session are the sensor signal of the disclosed system, sampled at 500 Hz, as well as the cuff pressure values. FIG. 1 presents an example of the data obtained during a blood pressure sweep of the finger cuff's internal pressure as well as the results of its processing. FIG. 1A of the figure displays the amplitude response versus time of the CT's sensor signal during the sweep. This provides a graphical display of the artery's response to varying pressure-based interrogation, which is displayed in FIG. 1B, i.e. the corresponding time evolution of the directly and simultaneously measured pressure steps. FIG. 1C displays the resulting oscillometric profile, or hill of signal amplitude versus pressure. This oscillometric profile is the initial data used by the initial analysis algorithm that is the basis of the subsequent blood pressure determination, along with the average values for systole and diastole obtained by the clinicians (vertical red bars) representing the Gold Standard in this case, and the corresponding pressure scan readings.

The initial analysis algorithm, which operates on the real-time data and can also process filed data, tracks the pump events, and performs heart beat peak detection in the in-between intervals and assembles the oscillometric hill profile, an example of which was shown in FIG. 1A-C. The positive-going and negative-going signals of the system derivative signal are tracked separately. Upon conclusion of the scan the algorithm performs a spline fit on the data, resulting in a combined oscillometric hill profile.

Figure 3:
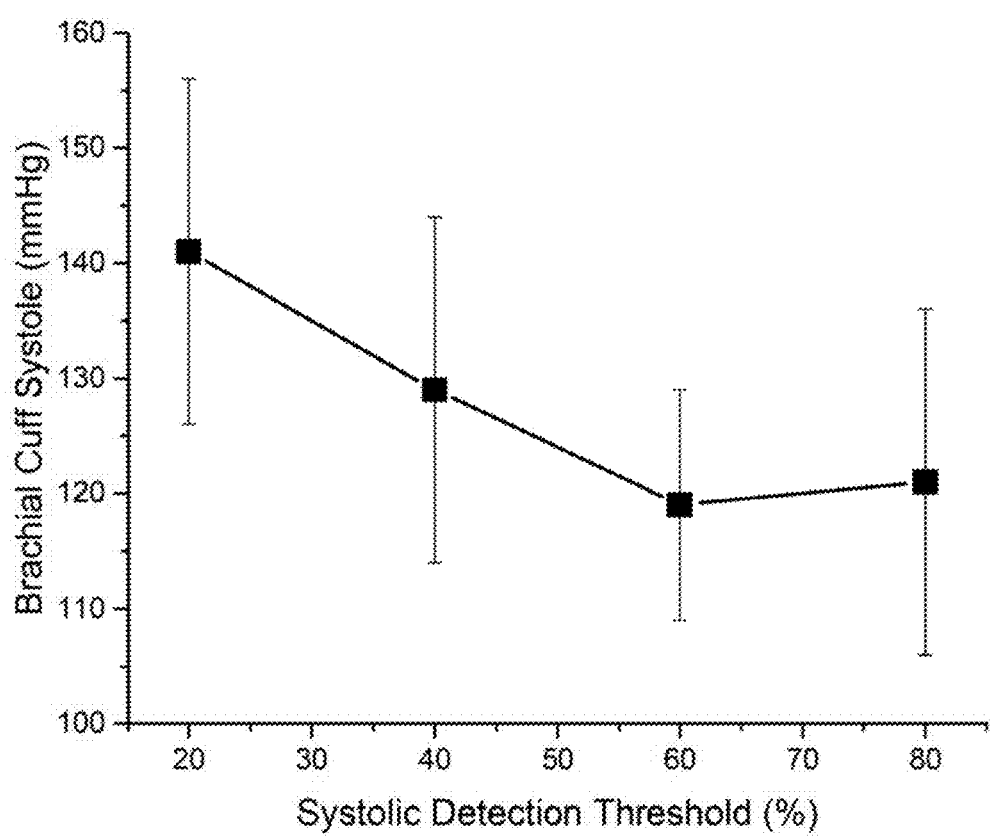
FIG. 3 shows clinically measured brachial systolic cuff pressure versus percentage systolic threshold according to an embodiment of the present invention.

The above information is used to detect trends in the characteristic thresholds as a function of pressure and as a function of steepest slopes of the oscillometric hill, profile, FIG. 3 gives an example presenting the clinically measured brachial systolic cuff pressure versus the percentage systolic threshold of the oscillometric hill profile, subject to the constraint that the two agree, for a given reading, within at least 8 mmHg. Only four threshold percentages are being considered in this example, 20%, 40%, 60% and 80%. The trend in the data indicates that, with increasing systolic blood pressure, the most probable detection threshold, as a percentage of the full height of the oscillometric hill, moves to lower thresholds, i.e. the tail on the high-pressure side becomes more and more important systole increases.

Figure 4:
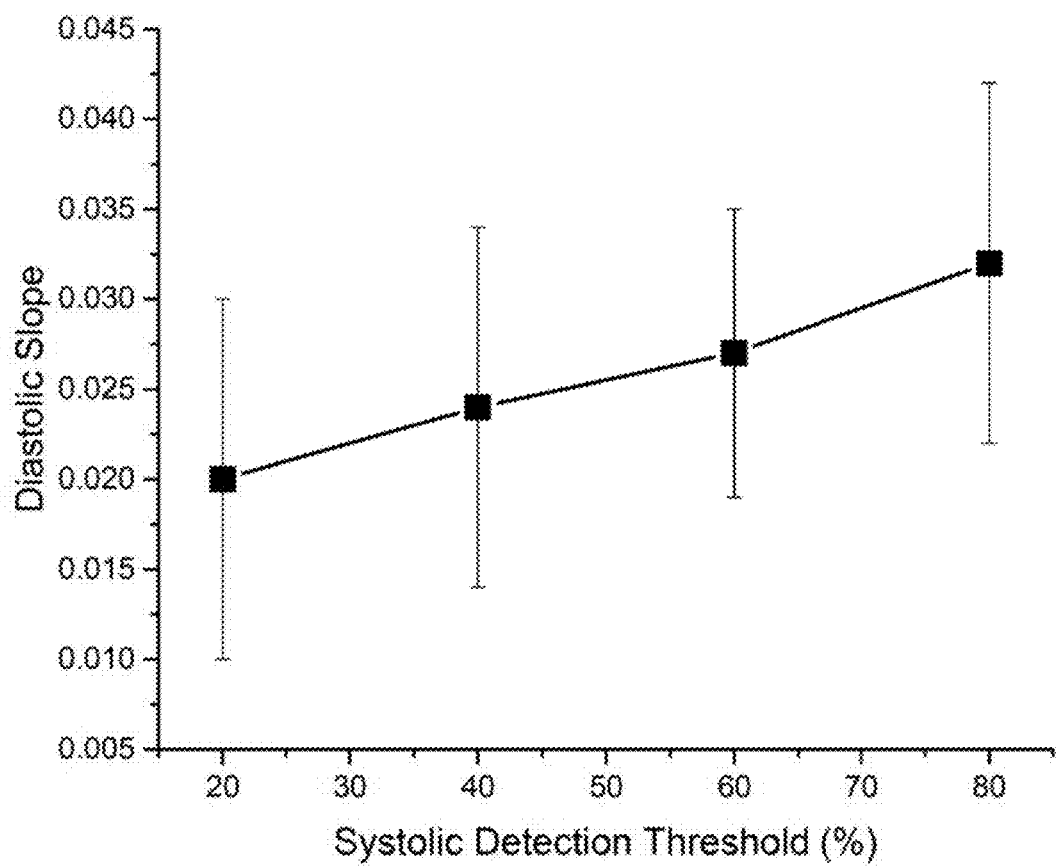
FIG. 4 shows the effect of diastolic side slope on systolic detection threshold.

FIG. 4 displays the effect that changes in the hill profile slope on the diastolic side have on the systolic detection threshold, subject to the same previous constraint. The trend illustrates that, as the slope increases, which is indicative of higher arterial compliance and/or better coupling to the arterial pulsations, the optimum systolic detection threshold moves to higher levels.

These trend responses set forth in FIGS. 2-4 are now parameterized and incorporated into the blood pressure extraction algorithm that compensates for cuff coupling issues, arterial stiffness, tissue compliance, and assesses spectral content of arterial pulse and slopes of the oscillatory profile.

The actual extraction of blood pressures from the oscillometric hill profile is then accomplished through an iterative process that entails a preliminary determination of diastolic and systolic pressures at the fixed percentage thresholds of 20%, 40%, 60% and 80%. The resulting set of pressure values allow a preliminary determination of the slopes, the approximate pulse pressure, and the range of the systolic slope. This makes it possible to determine whether this is a hypo-, normo- or hyper-tensive case and to move the systolic threshold accordingly (lower for higher pressures). Determination of the oscillatory amplitude for positive and negative-going components of the system's derivative signal provides information on the degree of coupling, which for the same pressure will move the threshold higher.

The next important coupling issue concerns the identification of tissue compliance and tissue thickness, which will determine the onset response of the digital arteries in the low-pressure realm of the oscillometric hill. Qualitatively put, if the intervening tissue is thick or tough as the sensing bladder expands toward the digital arteries, the arterial oscillatory response will be muted and the change in the oscillatory response from one pressure step to the next. i.e. the slope, will be very shallow. Practically speaking, it can take more than to 100 mmHg in bladder pressure until the diastolic response part of the oscillometric hill is reached, even though the subject's diastolic pressure is 70 mmHg. This clearly indicates that the "extra" pressure was required to push through the intervening tissue to engage the digital arteries.

The successful solution here has been to obtain clinical data from a cohort of subjects and to derive empirical relations based on the onset responses of this subject set, both in response amplitude and response slope, of the oscillometric hill in the 20-40 mmHg pressure range.

The next critical feature that has to be incorporated into the analysis is arterial stiffness. The approach is based on the observational fact that distinguishes the arterial pressure pulses associated with stiff arteries from those associated with flexible arteries: pressure pulses from flexible arteries are featured, while the pressure pulses from stiff arteries are less featured, or not at all. The features are due to the fact that arterial pulse envelope consists of several component pulses, specifically the left ventricular ejection pulse and two time-delayed reflection pulses. The presence or relative absence of these component pulse features relates to arterial stiffness as follows: the higher the arterial stiffness, the longer the rise time of any blood pressure variation. The arterial wall resists and delays the distensive effects due to each component pulse. Consequently the responses due the different component pulses will meld together, smoothed over by the wall's mechanical filtering effect. One approach to quantify this featuredness is to examine the spectral content of the arterial pressure pulse, the motivation being that the more featured the pulse is, the higher in frequency its spectral content will be. It is understood, however, that the strong mechanical filtering of the arteries sets strong boundaries to this approach. Specifically, physiological research has shown that the human arterial pulse has no spectral content past 15-20 Hz. For the approach discussed here it turns out that examining the frequency range between 1 and 10 Hz is sufficient. Specifically, it is possible to define a spectral content parameters that is defined by the ratio of the summed magnitude of a Fourier Transform between 6 and 10 Hz and the summed magnitude between 1 and 5 Hz that is useful in assessing the effect of arterial stiffness on shifts in the blood pressure thresholds on the oscillometric hill.

Figure 5:
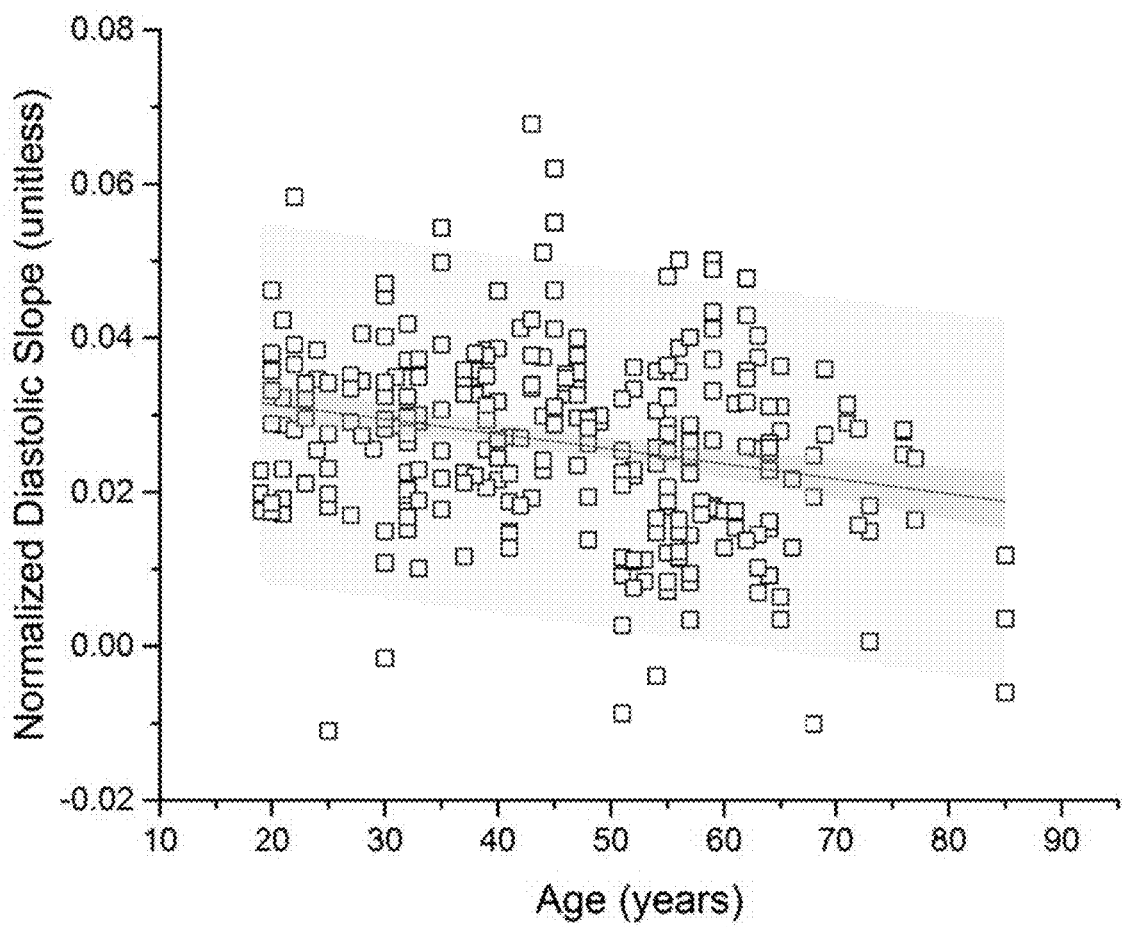
FIG. 5 shows the dependence of the spectral content parameter on, cohort age according to an embodiment of the present invention.

As a preliminary assessment of the physiological relevance of the model's spectral parameter, its age dependence was assessed. For example, FIG. 5 displays the age dependence of the spectral content parameter in a cohort of 140 subjects with a broad distribution in age and blood pressures. Since the increasing stiffness of older arterial walls smooths the structural features of the pulse compared to those of younger, more elastic arterial walls, a negative trend is expected with age. A statistically significant negative trend is indeed observed in the data.

Figures 6A, 6B:
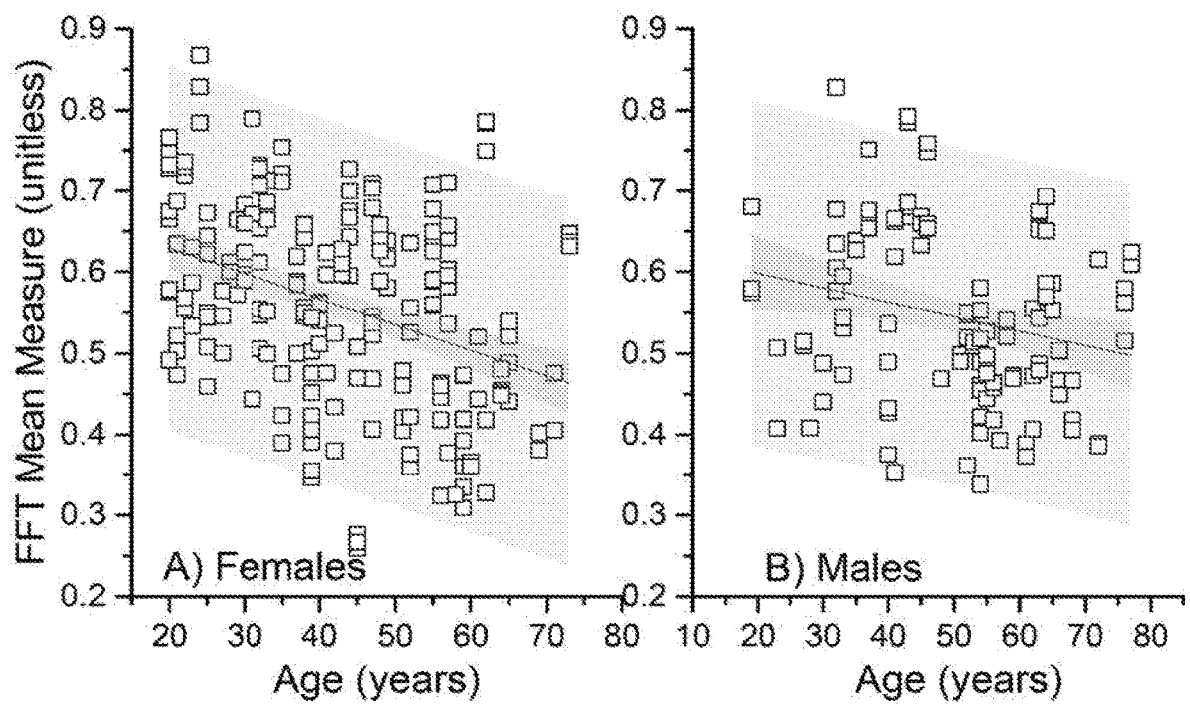
FIG. 6A shows the age dependence of the spectral content parameter for females according to an embodiment of the present invention.
FIG. 6B shows the age dependence of the spectral content parameter for males according to an embodiment of the present invention.

FIG. 6 displays the results of further categorizing the spectral content parameter according to sex. While both groups display the same trend, it is approximately twice as a large in females (FIG. 6A) as in males (FIG. 6B) This result may be related to the fact that females, on average, have lower arterial stiffness than males.

In a similar manner the slopes of the oscillometric profile can be assessed, since, based on the considerations above, they should be sensitive to changes in arterial stiffness, and should therefore trend with age.

Figure 7:
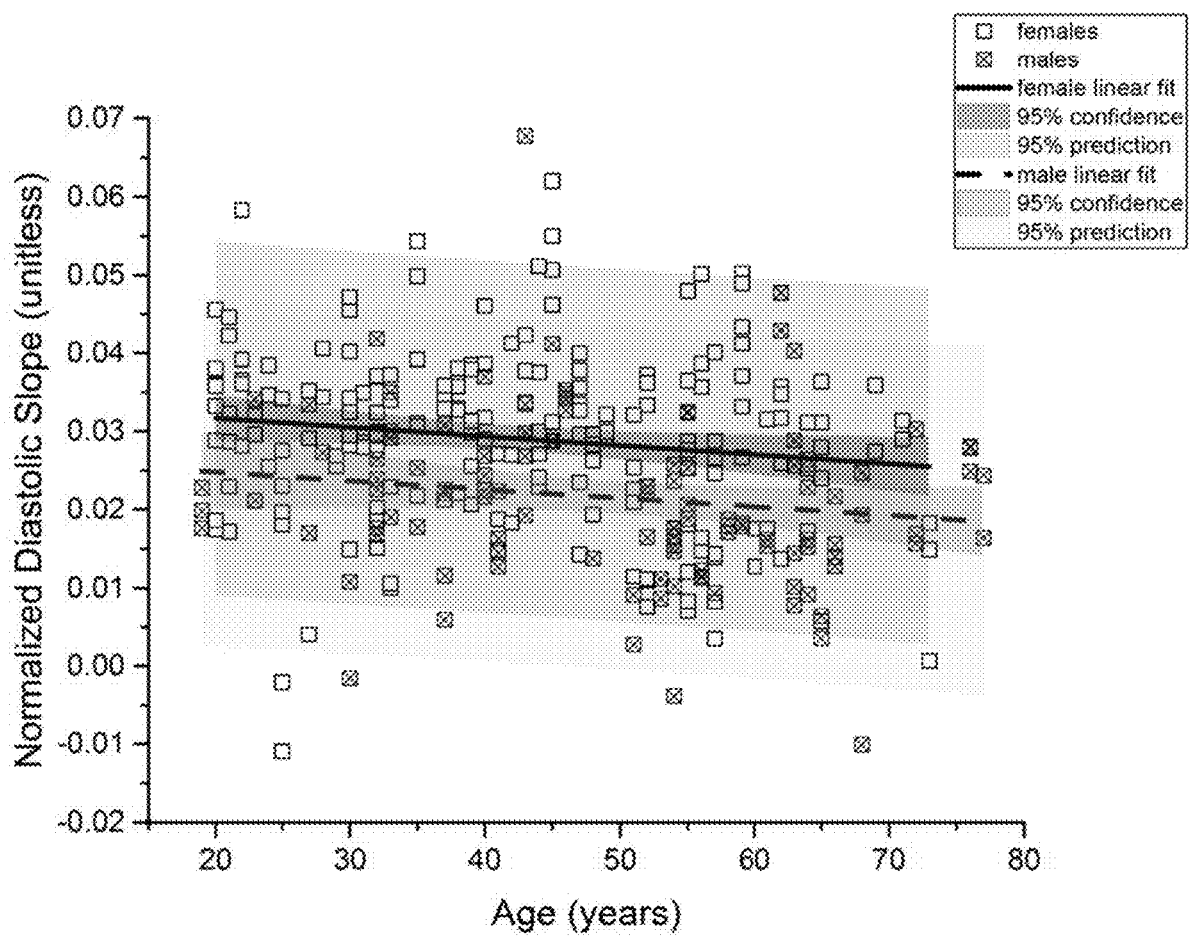
FIG. 7 shows the age dependence of the normalized diastolic slope of the oscillometric profile according to an embodiment of the present invention.

FIG. 7 displays the age dependence of the diastolic slope normalized against mean arterial pressure and categorized according to sex. The expected negative age trend is evident for both groups illustrating that with increasing arterial stiffness and age, the slope amplitudes decrease. Furthermore, and in agreement with the expected group difference in arterial stiffness between males and females, the diastolic slopes of the males as a group are lower than those of the females.

The situation is less clear with regard to the slopes of the systolic side of the oscillometric profile. FIG. 8A-C displays the overall age trend of both sexes (A) as well as the trends categorized by sex (B & C). The trends in the overall group and the females agree with expectations. Since the slopes are negative, the expected trend is positive, toward less negative slope values. For the male group (graph SC), however, the trend is essentially zero.

Figure 9A:
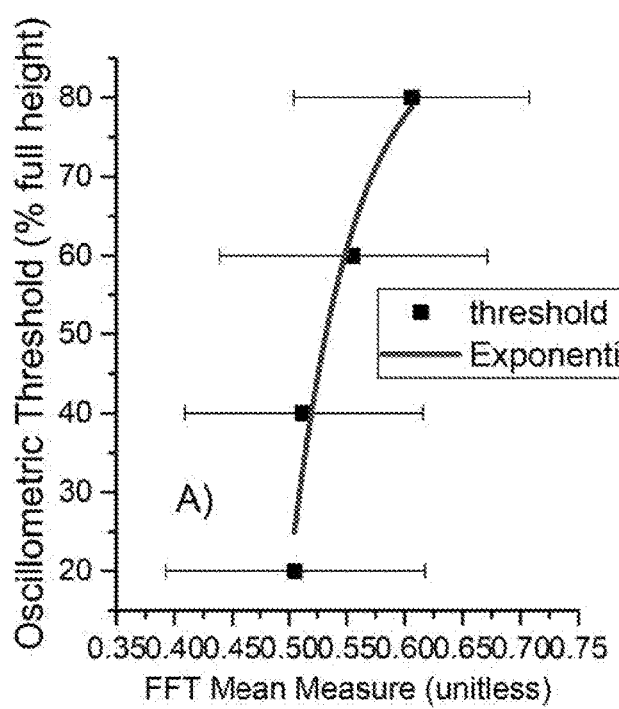
FIG. 9A shows the displays the results of determining the optical systolic slope, threshold, according to an embodiment of the present invention.

An example of how the systolic threshold, for example, depends on the spectral content parameter is presented in FIG. 9A, which displays the results of determining the optimal systolic slope threshold, held to four values (20%, 40%, 60% and 80% of full height), for matching the clinicians' averaged systolic readings as a function of the spectral content parameter for a given patient. As illustrated the systolic threshold moves higher, i.e. to lower systolic pressures as the parameter increases. Model-wise these parameters are used to establish the thresholds on the oscillometric profile that determine systole and diastole.

Figure 9B:
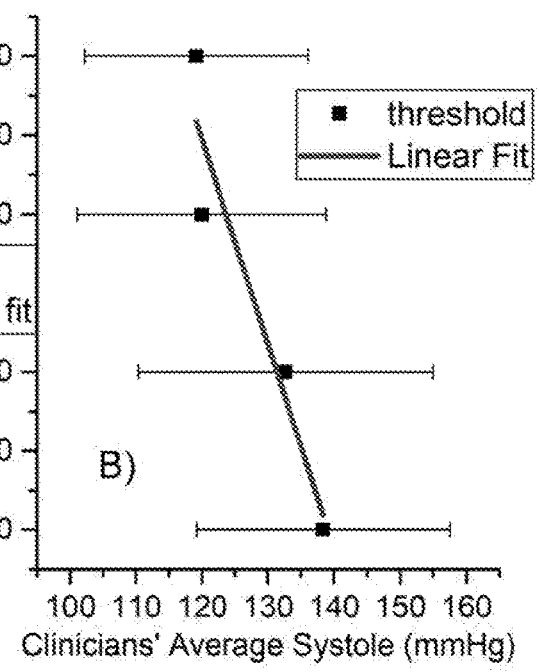
FIG. 9B shows the optimal threshold on the systolic side of the oscillometric profile of FIG. 9 A matching clinician's averaged systolic readings as a function spectral parameter according to an embodiment of the present invention.

FIG. 9B displays the results for obtaining the optimal match to the clinicians' averaged systolic readings, but as a function of the preliminary systolic reading. Put differently, the threshold for determining systole shifts depends on whether systole is high or low. The pronounced trend indicates that, as systole increases, the optimum threshold for determining an accurate value for systole shifts to lower levels of the oscillometric profile, i.e. to higher systolic pressures. In practice this is implemented by first obtaining a preliminary systolic reading to establish whether this is a low, medium or higher pressure case.

In what follows, an indirect, oscillometric arterial blood pressure monitoring system using a method of self-calibration is described. The self-calibration method provides the absolute starting or re-calibration blood pressure values against which a relatively continuous blood pressure monitoring mode will track changes in blood pressure.

Figure 10:
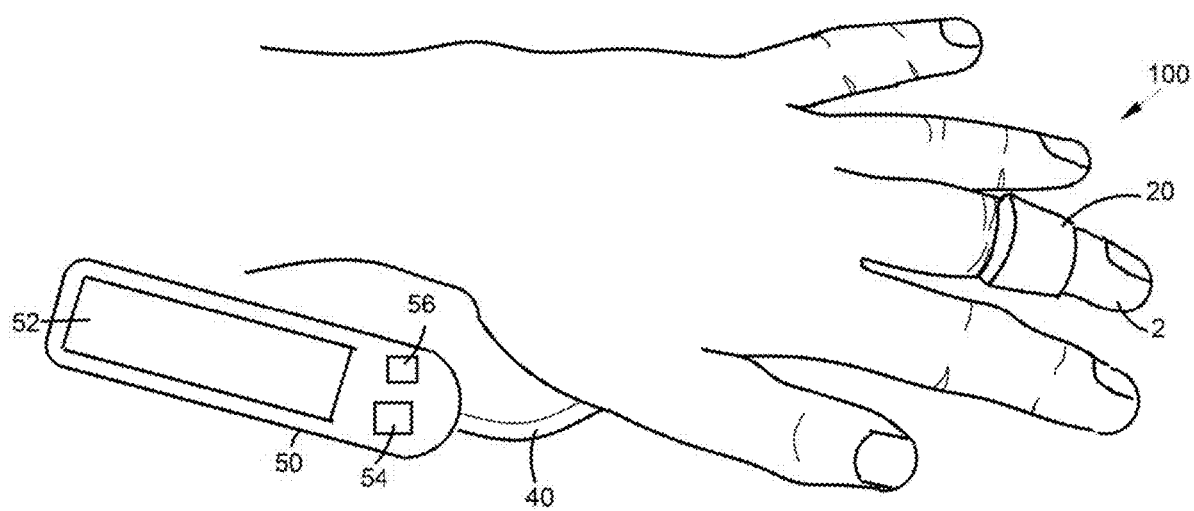
FIG. 10 shows an embodiment of an example finger cuff applied to the middle digit of a user and receiving module according to an embodiment of the present invention.

The example system 100 illustrated in FIG. 10 includes a finger digital cuff 20, receiving module 50 containing electronic circuitry (not shown), and mechanisms—in his embodiment pressure sensors 54 and 56—for controlling pressurization of the digital cuff 20. The electronic circuitry includes means for receiving and analyzing signals from the digital cuff 20 and outputting analysis results. Conduit 40 connects receiving module 50 and digital cuff 20 in pneumatic communication. Alternatively, electronic communication of signals between receiving module 50 and digital cuff 20 can be wireless, such as by providing communication means and a sensor, such as a piezo or relative pressure sensor, in close proximity to the artery being monitored.

From the receiving module 50, the data can be sent to any processing device used to gather and analyze data within the facility. The transfer of data can be through any means known at the time in the computer arts and applicable to the application. Alternatively, the data can be analyzed and read directly by a processing device within the receiving module 50. Optionally, receiving module 50 can include a display 52 on which data can be displayed and results of analysis can be displayed as outputs for reading.

The finger has a bone in the center and two arteries, one on, each side. The digital cuff 20 is placed on the finger 2 with a bladder 28 in contact with the skin overlying the two arteries. The bladder 28 is flexible and sealed on all sides to the substrate 26 and around the air conduit 40. Digital cuff 20 should preferably substantially conform to the shape of the finger on which it is placed so as to eliminate gaps and equally engage both finger arteries. As previously discussed, gaps will cause the bladder will expand into those voids in unpredictable ways, distorting the oscillometric hill that is analyzed to obtain calibrated starting blood pressures.

In the continuous blood pressure monitoring mode, upon pressurization of the bladder 28, through conduit 40, to a pressure less than the diastolic blood pressure of the user, the cylindrically pressurized digital cuff 20 squeezes the finger tissue hydraulically and partially unloads the finger arteries. The pressure required to perform the unloading may vary somewhat from patient to patient, but is typically within the range of 20 mm Hg to 60 mm Hg. Other effective ranges for some subjects are from 20 mm Hg to 40 mm Hg or from 30 mm Hg to 50 mm Hg. In each case, the pressure does not exceed the diastolic blood pressure of the user. This unloading makes a hydraulic coupling between the arteries and the flexible bladder 29. This eliminates the elasticity function of the artery, substituting the elastic restoring force of the bladder 28. That is, the bladder 28 carries out the function of the elastic arterial wall. The bladder 28 also now contains the pulse pressure wave. As previously stated, the bladder 28 has been pressurized to below the diastolic pressure.

FIG. 10 shows the digital cuff 20 attached around the middle finger 2 at the intermediate phalange, but could alternatively be attached to the proximal phalange of the middle finger 2. The proximal phalange of the thumb 3 is a poor site for calibration because the tendons interfere with obtaining a reliable oscillometric signal. Alternative positioning can be the middle or proximal phalange of the index, ring or baby fingers, though this positioning provides less optimal readings.

A standard, commercially available pressure sensor 54, such as a relative (gauge) or absolute sensor, can be used to keep the pressure in the digital cuff 20 constant and is no different from a manometer. The pressure sensor 54 is illustrated as being located within receiving module 50 in FIG. 11, but could alternatively be located in the digital cuff 20. When used in the digital cuff 20, it is used as a gage pressure sensor since it is open to the atmosphere on the other side. However, as the sole sensor, it does a poor job of measuring changes in pressure due to the pulse because of a lack of sensitivity to these very small changes in pressure, FIG. 12 shows an embodiment of digital cuff 20 having a hook section 22 affixed to interior side A and a loop section 24 affixed to exterior side B. The hook section 22 and the loop section 24 are affixed not only at opposite sides but also at both end of the substrate member 26 and are used to secure the digital cuff 20. It should be noted that the placement of the hook and loop, with respects to sides A and B, can be reversed. An inflatable bladder 28 is positioned on the interior side A of the substrate 26 approximately opposite the loop section 24 and contacts the users finger 2 (FIG. 10). In this embodiment, bladder 28 comprises an inflatable membrane 29 and receiving air conduit 40. The periphery of the membrane 29 is fused to the substrate member 26, as indicated at edges 32 and 34. The inflatable bladder 28 is configured to enable the sealed interior region 36 formed by the inflatable membrane 29 and the substrate member 26, to be pressurized to form, in conjunction with the conduit 40, a pressure sensor. The conduit 40 is in pneumatic communication with the interior region 36 and the electronic components receiving module 50 of FIG. 10.

FIG. 11 and FIG. 12 illustrate an example of a digital cuff 20, unwrapped in FIG. 11 and wrapped into a circular configuration in FIG. 12 to show the configuration in which it is used when wrapped around a finger. The hook and loop fasteners 22, 24 engage to maintain the digital cuff 20 in this configuration until the hook and loop fasteners are forcibly opened by pulling on the end of the substrate 26. In this figure, the interaction between the sealed edges 32 and 34 of the inflatable membrane 29 and conduit 40 of the bladder 28 to form a pressure sensor are illustrated.

The design of the digital cuff 20 is for illustration purposes and other digital cuffs meeting the same criteria can be used. The digital cuff 20 enables the system to be used, in continuous monitoring mode, without significantly affecting the flow of blood because the inflation of the digital cuff 20 need only be sufficient to produce a light coupling to the arteries of the finger 2. Below diastolic pressure, the digital cuff 20 does not change the inner diameter of the artery at all and therefore does not affect the flow of blood. In continuous monitoring mode the pressure in the digital cuff 20 is preferably less than the diastolic pressure in the artery, and preferably, no greater than about 50 mmHg (although may be somewhat higher, depending upon various factors of the subject, including, but not limited to diastolic blood pressure, fat content and other makeup of the finger, etc.). The lower limit of the pressure is sufficiently high to enable light coupling with the artery but coupling sufficiently low enough that there is no interference with the blood flow. In this way, the digital cuff 20 can be used for extended periods of time, that is, for multiple hours or days.

The digital cuff 20 is wrapped, around the measurement site and inflated to a low pressure less than diastolic pressure, but sufficient to increase the contact pressure. The pulse then causes a small variation in the internal pressure in the digital cuff 20 due to a very small volume change as the blood surges past the site of the digital cuff 20. In order to avoid occluding blood flow, the pressure is maintained below the diastolic pressure and is preferably in the range from 30 to 70 mmHg and most preferably in the range from about 35 to 55 mmHg, but may be within any of the other ranges mentioned heretofore. The pressure is determined on the basis of maintaining good contact with the finger 2, or more specifically, accurate monitoring of the pulse wave. The digital cuff 20 surrounds the phalange and applies uniform circumferential pressure. The pressure applied must be maintained within a range having a minimum and maximum, with exact values being determined based on the patient. The maximum level for the pressure must avoid occluding the blood flow while a minimum pressure is critical from the standpoint of maintaining good contact with the finger in order to sense the pulse pressure wave. A good operating range is 20-60 mmHg.

Figure 13:
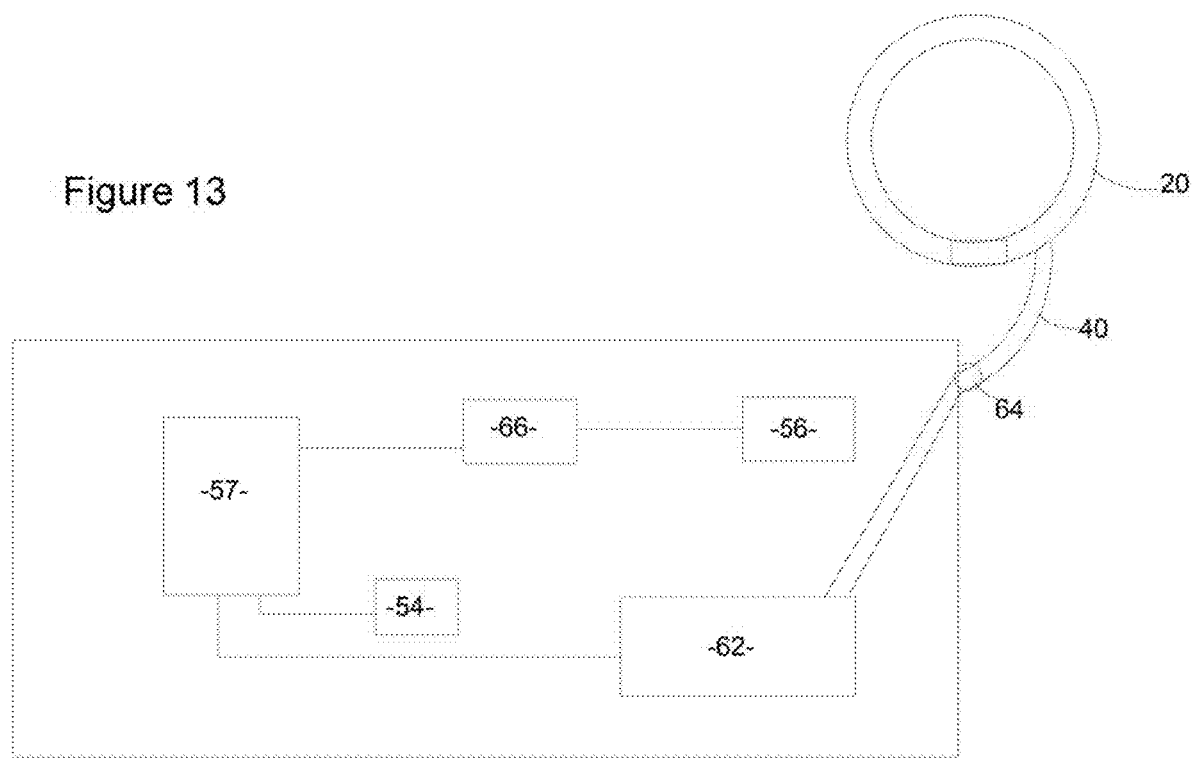
FIG. 13 is a schematic representation of the pressure control and monitoring elements of the system shown in FIG. 1, according to an embodiment of the present invention.

The schematic of FIG. 13 shows an example of the interior layout of the receiving module 50. The second pressure sensor 56, such as a piezoelectric disk element or equivalent, is electrically connected to a controller 57 comprising at least one processor configured to control operations of the system 100. Pump 62 is in pneumatic communication with digital cuff 20 via tube 40 and one-way valve 64. Pump 62 is electrically connected to controller 57, which controls operations of the pump 62 based on pressure reading feedback. Absolute pressure sensor 54 is also electrically connected to controller 57 and provides electrical signals to the controller 57 representative of the pressure sensed relative to atmospheric pressure, as one side of the sensor 54 is exposed to the atmosphere and the other side is exposed to the contained pressure space of the system 100 provided by digital cuff 20, tube 40, and the housing of the receiving module 50. The relative pressure sensor 56 is more sensitive than the absolute pressure sensor 54 and can be, for example, a piezo device formed of lead-zirconate titanate (PZT) deposited on a circular substrate, made of brass or stainless steel, or its equivalent. The relative pressure sensor 56 is mounted in a manner so that the normal room air is on one side and the pressurized system is on the other, causing the disk to bulge out. The bulging motion causes charge separation in the PZT which has been deposited onto the brass or stainless steel disk. For a constant pressure, this separation will be distributed by ordinary high resistance conduction. Once the pump 62 pressurizes the system to a constant desired pressure small pressure variations can be measured by the amplifier 66. Ideally, any leakage from the pneumatic connection or receiving module 50 housing, will be on the order of one pump cycle per quarter hour. The pressure oscillations originate in the digital cuff 20 which has effectively unloaded the arteries of the finger. The artery, by bulging out in proportion to the blood pressure, causes slight fleeting changes in the pressure of the trapped volume organized by the system 100. This slight change causes the PZT to bulge which causes charge separation which is converted to voltage by the transimpedance amplifier 66, which is inputted to the controller 57 to convert the voltage to a relative pressure change reading. The pressure readings can then be outputted by the controller 57 to display 52 and/or an external computing device according to any of embodiments described herein. The bandwidth of the device is adjusted slightly to remove sensitivity to outside noise sources. The signal bandwidth contains the fundamental frequency at about 1 Hz (the heart beat) and the signal features which extend to about 20 Hz. The raw data is ported directly to one of the processor's A/D inputs in the receiving module 50. Preferably, the processor then uses PDA to extract the parameters. Alternatively, the digitized raw data stream is telemetered to a computing device for extraction of the parameters.

The pulse decomposition analysis (PDA) principle is used to analyze the arterial pressure pulse. For a full disclosure of PDA technology see U.S. Pat. No. 7,087,025, Blood Pressure Determination Based on Delay Times between Points on a Heartbeat. Pulse, pending patent application Ser. No. 13/231,703, filed Sep. 13, 2011, U.S. Pat. No. 8,100,835, issued Jan. 24, 2012, PCT/US10/43914, filed Jul. 30, 2010, all of which are hereby incorporated herein, in their entireties, by reference thereto.

The basic components of the PDA algorithm are: 1) a peak finder that identifies heartbeats in the derivative data stream, 2) a differentiator that produces the second derivative of the detected heart beat which is then used to find the inversions corresponding to the locations of the component pulses, 3) a digital integrator, implemented as a Bessel filter, that generates the integrated pulse wave form from the differentiated raw signal stream, and from which relative component pulse amplitudes are determined, and 4) a low-pass filter that enables identification of the primary systolic peak. Furthermore the frequency content of the data stream is continuously analyzed in order to calculate signal to noise (S/N) figures of merit that determine whether signal fidelity is sufficiently high to permit peak detection and analysis.

Once the temporal locations of the reflection component pulses and the systolic pulse are identified, the T13 interval, the time delay between systolic (P1) and iliac peak (P3), is calculated. The P2/P1 ratio is calculated using the amplitudes of the P2 peak and the systolic peak, in the integrated pulse spectrum.

The system of the present invention operates passively at a low constant coupling pressure such as 40 mmHg, or one of the other pressures below diastolic blood pressure, mentioned above. The system 100 tracks blood pressure by analyzing the timing and amplitudes of the primary left ventricular ejection pulse as well as the arterial pulse reflections, at the phalange of the finger 2 around which the digital cuff 20 is wrapped.

Unlike previous systems, the present system can non-invasively provide absolute, real-time, beat-to-beat pressure measurement values if it is calibrated initially and at periodic intervals.

The finger cuff system 100 can be controlled from and stream data to the software running on any applicable computing device. Communication can be wireless using, for example, the Bluetooth transmission protocol. In a preferred embodiment, the finger cuff system 100 can automatically upload data by radio transmission (e.g., cell phone communication) to a cloud-based server on the Internet. In a preferred embodiment the digital sensor features a miniaturized design based on a piezo-electric sensor, weighs about 100 grams and runs for about 20 hours on a single battery charge.

Since the system 100 tracks pulse reflections that stem from the central arteries, it can be shown to be capable of tracking central blood pressure. Further the technology has been shown to be suitable as a hemorrhage detector.

The system's signal quality is sufficiently high as to enable detailed contour analysis, of the radial or digital pulse shape, which is influenced by factors such as systolic and diastolic blood pressure, and arterial stiffness. Specifically, it makes the resolution of the component pulse structure of the radial/digital pulse envelope possible.

Figure 14:
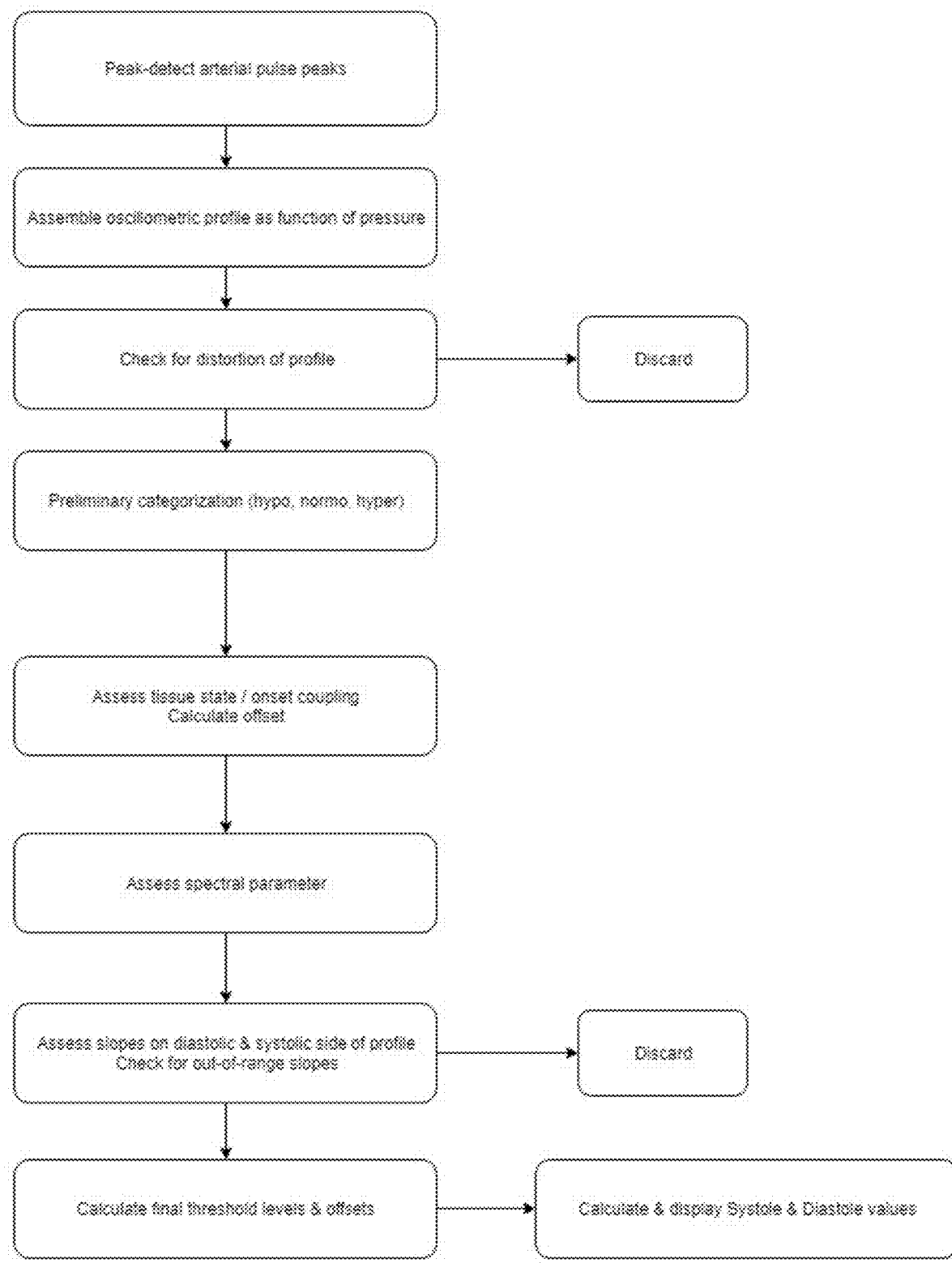
FIG. 14 shows the sequence of algorithmic processing events for a self-calibration or re-calibration event

The sequence of algorithmic processing events required for the system to perform a self-calibration or a re-calibration is shown schematically in FIG. 14. The required oscillometric profile is established through the peak detection of the arterial pulse subject to the different pressure scan steps. The result is the oscillometric profile as a function of pressure. As a first processing step, the oscillometric profile is tested for irregularities that can arise if the finger cuff was not applied symmetrically or if motion artifacts compromised the arterial pulse signal during the pressure scan. This will typically result in a multi-peaked oscillometric profile. If this condition is detected the profile is rejected and an error condition is displayed. If the profile is accepted the next processing step involves determining preliminary threshold values for systole and diastole, preferably at, respectively, 70% and 50% of the maximum amplitude of the profile. Based on these preliminary systole and diastole values the oscillometric profile is categorized into a likely low, normal, or high blood pressure scan. Specific values for the ranges are less than 25 mmHG for low, 26-40 mmHG for normal, and 40+ mmHG for high and an offset for systole is added depending on the classification, specifically 0, 10, 15 mmHG. No offset is calculated for diastole, based on analysis of clinical cohort data. In a next processing step the tissue coupling is estimated by assessing the maximum amplitude of the oscillometric profile and the systolic slope of the oscillometric profile in the low pressure range in order to calculate the offset that has to be subtracted from the ultimate blood pressure values due to the excess pressure that was required to penetrate the intervening tissue to engage the arteries. The range of pressures examined is usually between 20-40 mmHg, with the offset in the range from 0-30 mmHg. The next processing step assesses the spectral content of the arterial pulse at the different pressure steps of the oscillometric scan, the most important being the spectral content in the low and the intermediate pressure regime around the peak of the oscillometric profile of the original scan. In flexible arteries the spectral parameter will be high in the low pressure regime, where the pulse is not yet distorted by the applied pressure, for reasons discussed. Elastic arteries will also exhibit earlier collapse in the pressure profile, indicated by a significant decrease in the spectral parameter, than less flexible arteries. Specific values for the spectral parameter will be in the 0.6 or higher range for flexible arteries and 0.5 or lower for stiffer arteries. For values in between, this processing step is ignored because in this range the effect of the spectral parameter correction is minimal Finally the slopes of the diastolic and systolic side of the oscillometric profile are assessed for the determination of the final systolic and diastolic thresholds. This also provides a final quality control checkpoint, for if the slopes are unreasonably low, the scan can still be rejected. Acceptable slope ranges, normalized to the height of the oscillometric profile, are −0.04−−0.02 for systole and 0.01-0.05 for diastole. Based on the inputs of the described processing stages the final thresholds for systole and diastole are calculated, as well as offsets that will be applied to the values obtained. Threshold ranges are bracketed, respectively with regard to systole and diastole, between 80%-60% and 55-75% of the maximum oscillometric profile height.

With reference to FIG. 14 and specifically the calculation of the final threshold levels and offsets to obtain values for systole and diastole, equations 1-10, set forth below, provide a quantitative framework for the analysis that was described above. The goal, i.e., equations 9 and 10, is to obtain the threshold levels, in percentages of the full height of the oscillometric curve (OC) for both systole and diastole, i.e., respectively, thresh $\%_{systole}$ and thresh $\%_{diastole}$. OC, an example of which is displayed in FIG. 1, is a curve that is a function of pressure so that OC(thresh $\%_{systole}$), for example, is the pressure corresponding to the curve point identified by thresh $\%_{systole}$ on the systolic side of OC. The corresponding identification applies to thresh $\%_{diastole}$ on the diastolic side of OC. To the resulting pressures obtained from OC are added the offsets offset$_{tissue,systole}$ and offset$_{tissue,diastole}$, calculated to compensate for the tissue compression that is required to reach the arterial wall.

The threshold levels thresh $\%_{systole}$ and thresh $\%_{diastole}$ are calculated using equations 1 and 2, i.e. both are equal to a default threshold on the respective sides of the OC, as expressed by equations 3 and 4. These default thresholds for systole and diastole are now modified by the contributions due to the spectral parameter, $\Delta\%_{SP.systole}$ and $\Delta\%_{SP.diastole}$, and the slope parameters, $\Delta\%_{SL.systole}$ and $\Delta\%_{SL.diastole}$. These threshold modulation parameters in turn are modeled on a linear dependence with the underlying physiological parameter, as presented in equations 5 through 8.

$$\text{thresh } \%_{systole} = \text{default } \%_{systole} + \Delta\%_{SP.systole} + \Delta_{SL.systole} \quad (1)$$

$$\text{thresh } \%_{diastole} = \text{default } \%_{diastole} + \Delta\%_{SP.diastole} + \Delta_{SL.diastole} \quad (2)$$

$$\text{default } \%_{systole} = 80\% \quad (3)$$

$$\text{default } \%_{diastole} = 70\% \quad (4)$$

$$\Delta\%_{SP.systole} = \alpha_{SP.systole} SP \quad (5)$$

$$\Delta\%_{SP.diastole} = \alpha_{SP.diastole} SP \quad (6)$$

$$\Delta\%_{SL.systole} = \alpha_{SL.systole} SL_{systole} \quad (7)$$

$$\Delta\%_{SL.diastole} = \alpha_{SL.diastole} SL_{diastole} \quad (8)$$

$$\text{Systole} = OC(\text{thresh } \%_{systole}) + \text{offset}_{tissue.systole} \quad (9)$$

$$\text{Diastole} = OC(\text{thresh } \%_{diastole}) + \text{offset}_{tissue.diastole} \quad (10)$$

Receiving module 50 is configured to operate digital cuff 20 to function as an oscillometer and to generate signals representative of absolute systolic and diastolic blood pressure of the subject when in contact with the finger 2 or another finger. In this mode, digital cuff 20, conduit 40, and receiving module 50 make up an oscillometric sphygmomanometer configured to automatically take absolute systolic and diastolic blood pressure readings when controlled to do so by receiving module 50. Conduit 40 interconnects digital cuff 20 and receiving module 50 both pneumatically and electrically, so that receiving module 50 can automatically inflate digital cuff 20 and control inflation levels properly to obtain absolute systolic and diastolic blood pressure readings. To take absolute systolic and diastolic pressure readings of the subject, the receiving module 50 automatically pressurizes the digital cuff 20 at a time determined by programming in the receiving module 50. The receiving module 50 controls a compressor to generate air pressure to inflate the digital cuff 20 step-wise as previously described, generating an oscillometric hill that is then analyzed subject to the slope and amplitude conditions previously described. Receiving module 50 includes a processor configured to receive the signals from the sensor(s) of first digital cuff 20. To provide adequate coupling of the digital cuff 20, the air bladder within digital cuff 20 has to be uniformly supported by a semi-cylindrical enclosure that is rigid enough to pressure-contain the air bladder so that increases in inflation pressure of the cuff from the receiving module are entirely directed to the digital arteries and not elsewhere, and likewise arterial pressure modulations induced in the cuff are contained and entirely directed to conduit 40.

Using the absolute systolic and diastolic blood pressure readings previously obtained, the processor calibrates a processing algorithm, such as the PDA algorithm for the continuous tracking of blood pressure, used to process signals from the cuff 20 when the pressure applied by the cuff is below diastolic blood pressure of the subject. The system 100 then proceeds with blood pressure wave form monitoring of the subject in real time, with the cuff 20 at a pressure below diastolic blood pressure of the subject, providing real time, beat-by-beat, absolute systolic and diastolic blood pressure measurements.

FIG. 14 illustrates events that can be performed by the system 100 for self-calibrating the system to make absolute systolic and diastolic measurements of a subject via the cuff 20. At event 602 the receiving module 50 controls finger cuff 20 to function as an oscillometric device in a manner as described above and receives information regarding the subject's blood pressure. At event 604, receiving module 50 converts signals received from cuff 20 that are representative of absolute systolic and diastolic blood pressure readings to absolute systolic and diastolic blood pressure values. Using the absolute systolic and diastolic blood pressure readings and signals received from operation of cuff 20, the processor calibrates a processing algorithm used to process signals from the finger cuff 20 when cuff 20 is at a pressure below diastolic blood pressure so that processing of signals from cuff 20 provides absolute systolic and diastolic blood pressure readings. Once the self-calibration process has completed, at event 606 the system 100 can proceed with monitoring blood pressure wave forms of the subject, including, but not limited to monitoring in real time, using signals received from cuff 20 and processed by device 50 using the self calibrated processing algorithm, including the ability to make real time, beat-by-beat, absolute systolic and diastolic blood pressure measurements.

Figure 15:
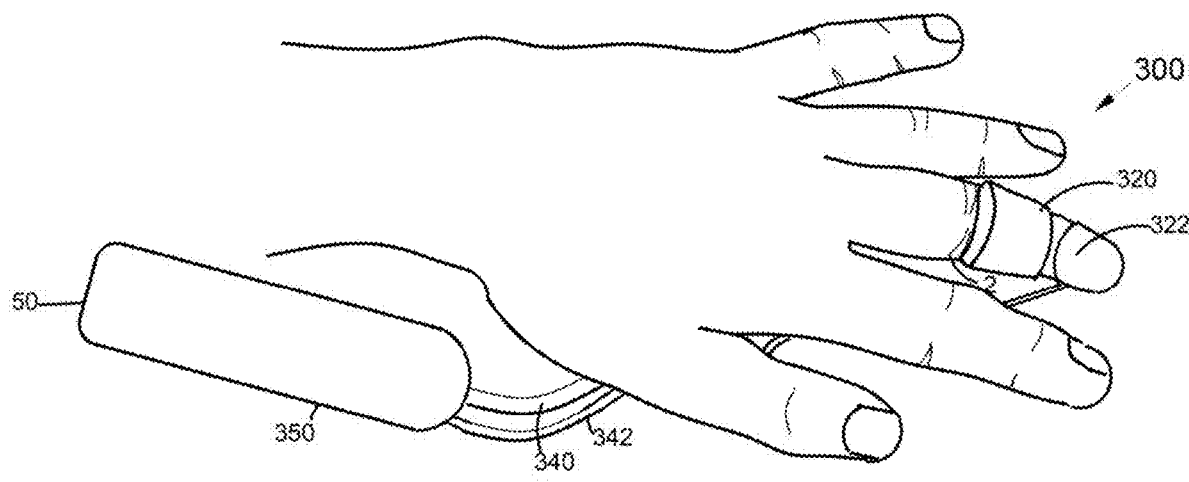
FIG. 15 illustrates an alternate embodiment of the disclosed system including a patch or bandage for providing pulse oximeter readings according to an embodiment of the present invention.

FIG. 15 illustrates a self-calibrating system 300 for blood pressure wave form analysis according to another embodiment of the present invention. System 300 includes a first finger cuff 320 configured and dimensioned to encircle a finger 2 of a subject. Like the embodiment of FIG. 10, the first finger cuff may use the cuff 20, as described above or any of the other embodiments described in US Patent Application Publication No. 2012/0238887. The inflatable member of cuff 320 is configured to be inflated to apply pressure circumferentially to the finger at a pressure level below a diastolic blood pressure of the subject and includes at least one pressure sensor that is displaceable by pressure fluctuations transferred from the finger to the inflatable member to generate signals corresponding to blood pressure wave forms representative of blood pulses passing through the finger. Pressure fluctuation data is sent from the cuff 320 to the receiving module 350 via the tube 340.

A two-component system can be utilized wherein a finger cuff bladder is used to pressurize and sense the artery, but a distally located optical sensor, such as an optical plethysmograph, provides additional information on the state of the pressurization/modulation of the digital arteries. As shown in FIG. 15, a second finger cuff or cap 322 is configured to contact the finger by fitting over the distal end or tip of the same finger on which cuff 320 is installed. The second finger cuff or cap 322 includes an oxygenation sensor, such as a pulse oximeter (photoplethysmograph) as known in the art. The second cuff or cap 322 is configured, when placed on the distal tip of the finger as shown, to shine light through the fingertip and measure the spectral attenuation of the light. The spectral attenuation of the light has a direct relationship to the amount of oxygen in the blood that the light passes through and the amount of oxygen in the blood has a direct relationship to the subject's pulse. Signals representative of the level of spectral attenuation of the blood are transmitted from second cuff or cap 322 to receiving module 350 via electrical connection 342.

Figure 16:
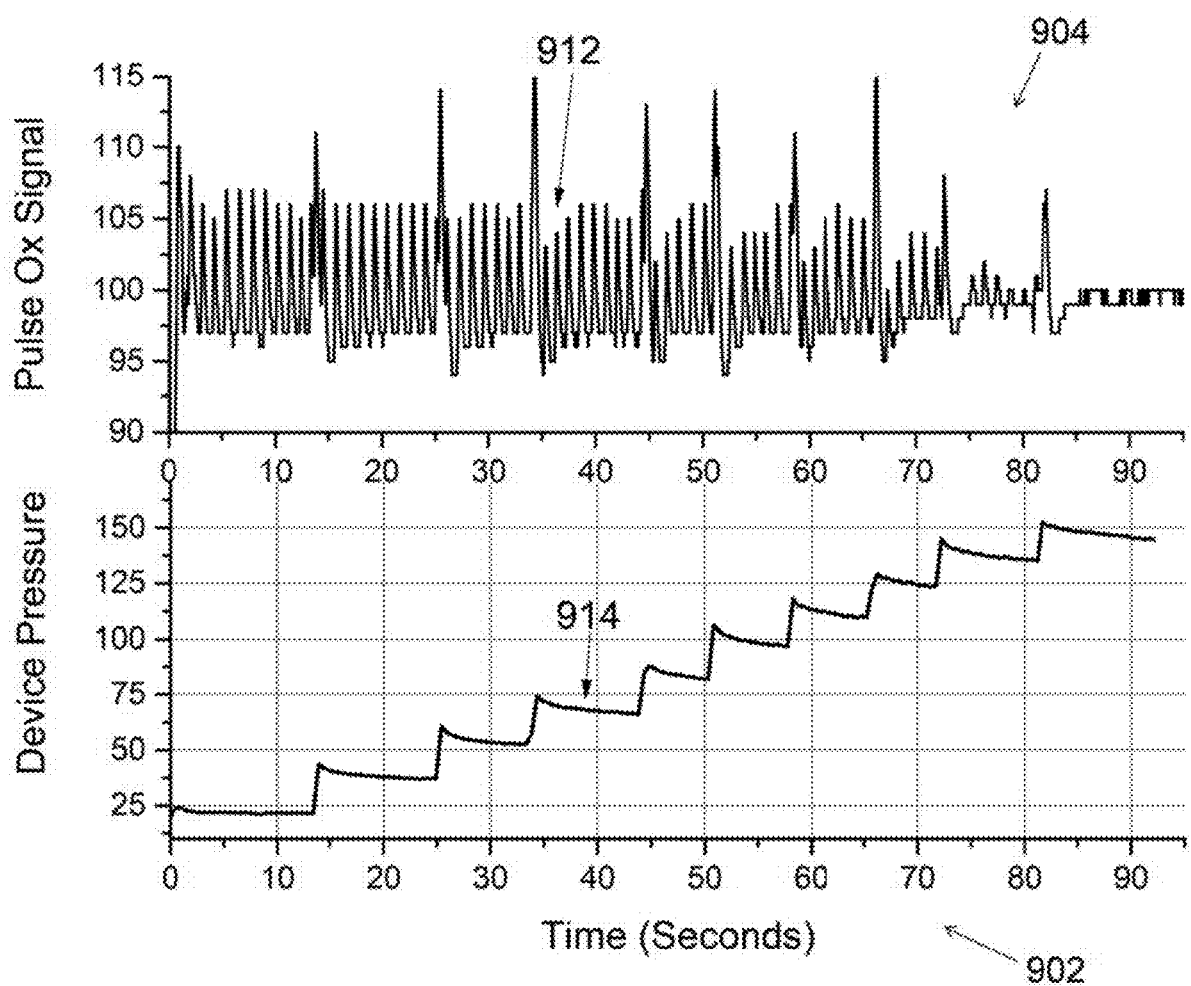
FIG. 16A-B shows graphs of inflation pressure of a cuff, graph 16A and pulse oximeter signals graph 16B, both plotted on the same time scale to show the relationship between the pressure of the cuff and the resultant pulse oxygenation signal, according to an embodiment of the present invention.

To take absolute systolic and diastolic pressure, readings of the subject, the receiving module 350 automatically pressurizes the cuff 320 at a time determined by programming in the receiving module 350. FIGS. 16A and 16B show graphs of inflation pressure of cuff 320 (graph 902) and pulse oximeter signal (graph 904) both plotted on the same time scale to show the relationship between the pressure of the cuff 320 and the resultant pulse oxygenation signal. The processor within the receiving module 350 controls a compressor to generate air pressure to inflate the cuff 320. As the cuff 320 is inflated (pumped up), the pressure rises step-wise with each cycle of the input of pressure into the cuff 320. Some overshoot 906 and relaxation 908 of the pressure value is evident with each step-wise increase, likely due to the elastic/plastic characteristics of the bladder 28, tubing 340, tissue of the finger, or any combination of these.

During the time that the pressure in the cuff 320 is below the diastolic blood pressure of the subject, the pulse oximeter signal remains substantially at a steady state value 910 (ignoring the overshoot and relaxation portion of the signal), which is to be expected, as there has been no inhibition of blood flow past the illumination site and therefore the blood oxygenation level remains substantially constant. When the pressure of the cuff 320 reaches the subject's absolute diastolic blood pressure, the overshoot begins to occlude the arteries in the finger 2 subject to the pressure from cuff 320, thereby lowering the pulse oximeter signal as the blood oxygenation level decreases as a result of the lessened blood flow due to the partially occluded arteries, and the relaxation sets the steady state pressure back to a pressure slightly lower than diastolic pressure so that the pulse oximeter signal improves over that pump cycle and stays steady, see 912. The corresponding time of occurrence of this event on the Device pressure chart indicates the absolute diastolic pressure, see 914, which, in this example is about 63 to 70 mm Hg.

As the cuff 320 continues to be pumped up beyond the diastolic pressure and the pressure of the cuff 320 reaches the absolute systolic pressure of the subject, the pulse oximeter signal reduces substantially and stays steady there, as indicated at 916. The corresponding time of occurrence of this event on the Device Pressure Chart 902 indicates the absolute systolic pressure, see 916, which in this example is slightly less than 150 mm Hg.

Receiving module 350 includes a processor configured to measure the pressure in the cuff bladder (28 in FIG. 11), as well as receive the signals from the sensor(s) of first finger cuff 320, as well as the signals from the second finger cuff/cap 322.

For self-calibration, a processor in receiving module 350 pressurizes the first finger cuff 20 in a manner as described above and, at the same time receives signals from the second cuff/cap 320 regarding the oxygenation of the subject's blood. The signals received from second cuff/cap 320 are monitored and analyzed, while at the same time monitoring the pressure of the first cuff 320 in a synchronized manner. In this way the absolute diastolic and systolic pressures can be identified by the processor of receiving module 350 in the manner described above.

After obtaining the absolute systolic and diastolic pressure readings, receiving module 350 immediately depressurizes cuff 320 to an operating pressure below diastolic blood pressure and receives signals from the cuff 320 that characterize the blood pressure wave forms of the subject in a manner as described previously with regard to system 100. These signals are used in combination with the absolute systolic and diastolic blood pressure readings by the processor to calibrate a processing algorithm used to process signals from the first finger cuff 320, at a pressure below diastolic blood pressure so that processing of signals from cuff 320 alone will provide absolute systolic and diastolic blood pressure readings. Once the self-calibration process has completed the system 300 can proceed with blood pressure wave form monitoring of the subject in real time, including the ability to make real time, beat-by-beat, absolute systolic and diastolic blood pressure measurements with the cuff 320 at a pressure below diastolic blood pressure. Other diagnostic values that can be calculated include, but are not limited to: heart rate variability and respiration rate, as well as any of the other diagnostic values described above.

Figure 17:
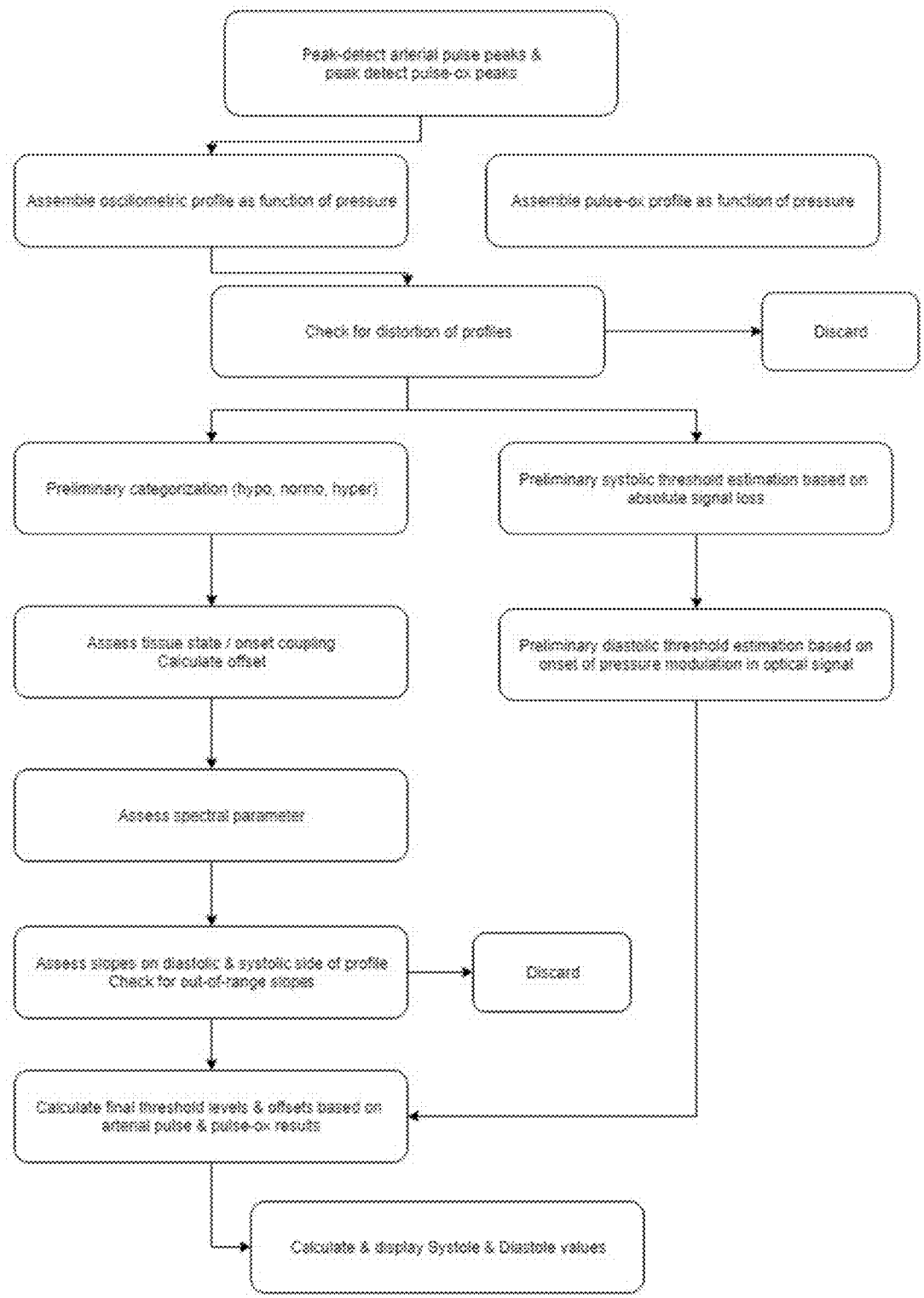
FIG. 17 is a schematic representation of the pressure control and monitoring elements of the system shown in FIG. 1, according to an embodiment of the present invention.

FIG. 17 illustrates events that can be performed by the system 300 for self-calibrating the system to make absolute systolic and diastolic measurements of a subject via the cuff 320. At event 1002 receiving module 350 pressurizes cuff 320, while monitoring the pressure of cuff 20 and simultaneously monitoring signals received from the second cuff/cap 322. At event 1004, receiving module 350 identifies absolute diastolic and systolic pressures from the processing of event 1002 in the manner as described above.

At event 1006, receiving module 350 reduces the pressure of cuff 320 to an operating pressure below absolute diastolic pressure of the subject and receives signals from the cuff 320 representative of the subject's blood pressure wave forms. Using the absolute systolic and diastolic blood pressure readings and signals received from operation of cuff 320, the processor calibrates a processing algorithm used to process signals from the first finger cuff 320, so that processing of signals from cuff 320 alone provides absolute systolic and diastolic blood pressure.

Once the elf-calibration process has completed, at event 1010 the system 300 can proceed with monitoring blood pressure wave forms of the subject, including, but not limited to monitoring in real time, using signals received from cuff 320 and processed by receiving module 350 using the self-calibrated processing algorithm. This includes the ability to make real time, beat-by-beat, absolute systolic and diastolic blood pressure measurements. Other diagnostic values that can be calculated include, but are not limited to: heart rate variability and respiration rate and any of the other diagnostic values noted above.

System 300 can be re-calibrated, as needed, in the same manner as described above. It must be noted that as used herein and in the appended claims, the singular forms "a", "a", and "the" include plural referents unless the context clearly dictates otherwise. Thus, for example, reference to "a pulse" includes a plurality of such pulses and reference to "the sensor" includes reference to one or more sensors and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The following articles are incorporated herein by reference as though recited in full.

[1] Nesselroad J M, Flacco V A, Phillips D M, Kruse J., Accuracy of automated finger blood pressure devices, Fam Med. 1996 March; 28(3):189-92.

[2] Veerman DP1, Lenders J W, Thien T, van Montfrans G A, LAM 100/Marshall F-88: accuracy and precision of a new device for discontinuous finger blood pressure measurement, J Hum Hypertens, 1993 April; 7(2):113-5.

[3] Lyew M A, Jamieson J W, Blood pressure measurement using oscillometric finger cuffs in children and young adults. A comparison with arm cuffs during general anaesthesia, Anaesthesia. 1994 October; 49(10):895-9.

[4] Lee J Y, Kim J K, Yoon G., Digital envelope detector for blood pressure measurement using an oscillometric method, J Med Eng Technol. 2002 May-June; 26(3):117-22.

[5] Babbs C F, Oscillometric measurement of systolic and diastolic blood pressures validated in a physiologic mathematical model, Biomed Eng Online. 2012 Aug. 22; 11:56. doi: 10.1186/1475-925X-11-56.

[6] Gizdulich P, Prentza A, Wesseling K H., Models of brachial to finger pulse wave distortion and pressure decrement, Cardiovasc Res. 1997 March; 33(3):698-705.

What is claimed is:

1. An indirect blood pressure monitoring system enabling self-calibration to obtain absolute blood pressure values comprising:

a digital cuff comprising an air bladder and a securing mechanism, said securing mechanism maintaining engagement between said cuff and a digit on which said cuff is positioned on a user, said digit having tissue overlying at least one artery, wherein, said cuff is positioned on said digit with said air bladder in contact with said tissue overlying said at least one artery;

a receiving module, having electronic components, in communication with said digital cuff, said receiving module configured to control operation of said digital cuff to take either absolute or relative blood pressure readings;

an air conduit in pneumatic communication with said digital cuff and said receiving module;

a pressure controlling means within said receiving module adapted to pump air through said air conduit into said air bladder and to sense changes in pressure detected by said air bladder, the pressure controlling means including at least one pressure sensor;

a processor connected to said receiving module, said processor configured to run an algorithm analyzing real-time pressure change data received from said digital cuff when taking absolute blood pressure readings in relation to filed pressure change clinical data, said algorithm extracting parameters affecting digital pulse pressure, establishing an oscillometric profile as a function of said air bladder pressure, and considering intervening effects on digital pulse pressure; and a display mechanism adapted to output analyzed pressure data from said processor;

wherein, after establishing the oscillometric profile, said processor is configured to maintain a pressure of said air bladder at a pressure less than said user's diastolic blood pressure, thereby circumferentially squeezing said digit to partially unload said at least one artery of said digit and creating a hydraulic coupling between said at least one artery and said air bladder;

wherein, said processor is configured to detect, via said hydraulically coupled air bladder of said cuff, pulse pressure oscillations caused by pulse pressure waves passing through said at least one artery of said digit of said user; and wherein, said at least one pressure sensor is configured to sense said pulse pressure oscillations for analysis by said processor; and wherein, said processor is configured to use said oscillometric profile to derive a calibrated, absolute blood pressure value against which a relatively continuous blood pressure monitoring mode will track changes in blood pressure.

2. The system of claim 1 wherein said intervening effects affecting pulse pressure include coupling of blood pressure monitoring device, number of arteries being monitored, arterial stiffness, tissue variations, filtering effects, pressure pulse amplification, and spectral content of arterial pulse.

3. The system of claim 1 wherein said processor analyzes said real-time pressure change data using a method of calibration comprising:
  i) detecting arterial pulse peak of said arterial pulse from oscillometric pressure scans;
  ii) deriving said oscillometric profile as a function of pressure from said arterial pulse peak, said oscillometric profile having a diastolic side, a systolic side, and a maximum amplitude;
  iii) testing said oscillometric profile for irregularities due to cuff positioning or scan errors;
  iv) rejecting or accepting said oscillometric profile based on presence or absence of the irregularities;
  v) determining preliminary threshold values for a systole and a diastole, said preferred values being 70% of the maximum amplitude of the oscillometric profile for the systole and 50% of the maximum amplitude of the oscillometric profile for the diastole;
  vi) categorizing the oscillometric profile into low, normal, or high blood pressure ranges based on said preliminary systole and diastole threshold values;
  vii) calculating a first offset for the systole based on said categorization;
  viii) estimating a tissue coupling by assessing said maximum amplitude and a systolic slope of said oscillometric profile in the low pressure range to calculate a second offset;
  ix) assessing the spectral content of the arterial pulse at different pressure steps of an oscillometric scan; and
  x) assessing a diastolic slope of the oscillometric profile;
  xi) calculating final systolic and diastolic thresholds, based on the diastolic slope and the systolic slope;
  xii) adding the first offset to the final systolic threshold and subtracting the second offset from the final systolic threshold and from the final diastolic threshold to produce said calibrated, absolute blood pressure values.

4. The system of claim 1 wherein said digit is a finger having a shape and having two arteries.

5. The system of claim 4 wherein said cuff is placed in a position on said finger that substantially conforms to the shape of said finger, said position eliminating gaps between said finger and said cuff, and said cuff equally engaging both of said two arteries.

6. The system of claim 1 wherein said air bladder of said digital cuff is uniformly supported by a semi-cylindrical enclosure sufficiently rigid to pressure-contain said air bladder, wherein said uniform support provides for said hydraulic coupling of said air bladder with said at least one artery.

7. The system of claim 6 wherein increases in an inflation pressure of the air bladder of said digital cuff from the receiving module are directed to said at least one digital artery by said hydraulic coupling.

8. The system of claim 6 wherein the pulse pressure oscillations induced in the cuff by arterial pressure waves are contained within said air bladder and directed to said air conduit.

9. The system of claim 1 wherein said air bladder pressure maintained after establishing the oscillometric profile is within the range of 20 mm Hg to 60 mm Hg.

10. The system of claim 9 wherein said air bladder pressure maintained after establishing the oscillometric profile is in the range of 35 mmHg to 55 mmHg.

11. The system of claim 1 wherein said processor is connected remotely from said receiving module.

12. The system of claim 1 wherein said processor is connected within said receiving module.

13. The system of claim 1 wherein said calibrated, absolute blood pressure values fall within guidelines set by ANSI/AAMI/ISO 81060-2:2013 standard.

14. A method of self-calibration of an oscillometric, digital blood pressure monitoring device to obtain an absolute blood pressure value comprising:
  i) positioning a digital cuff on a digit of a user said cuff having an air bladder and a securing mechanism, said digit having a tissue overlying at least one artery, said cuff positioned on said digit with said air bladder in contact with said tissue overlying said at least one artery;
  ii) maintaining engagement between said cuff and said digit with said securing mechanism;
  iii) controlling operation of said digital cuff with a receiving module having electronic components in communication with said digital cuff, said receiving module configured to control operation of said digital cuff to take absolute blood pressure readings;
  iv) pressurizing said air bladder of said digital cuff with a pressure controlling means within said receiving module, said pressure controlling means adapted to pump air into said air bladder through an air conduit in pneumatic communication with said digital cuff and said receiving module; wherein, after establishing the oscillometric profile, said air bladder is maintained at an air bladder pressure less than diastolic blood pressure of said user, thereby circumferentially squeezing said digit to partially unload said at least one artery of said digit and creating a hydraulic coupling between said at least one artery and said air bladder;
  v) sensing pulse pressure oscillations detected by said hydraulically coupled air bladder with at least one pressure sensor of said pressure controlling means, the pulse pressure oscillations caused by pulse pressure waves passing through said at least one artery of said digit of said user;
  vi) transmitting pressure oscillation data associated with the pulse pressure oscillations to a processor connected to said receiving module;
  vii) deriving a calibrated, absolute blood pressure value by performing an analysis of said pressure oscillation data received from said digital cuff with the processor using a pulse decomposition analysis to extract parameters affecting digital pulse pressure and to acquire an oscillometric profile as a function of pressure, wherein said analysis comprises the steps of:
    a) performing oscillometric pressure scans to detect arterial pulse peak to derive said oscillometric profile as a function of pressure, said oscillometric profile having a diastolic side, a systolic side, and a maximum amplitude;
    b) testing said oscillometric profile for irregularities due to the digital cuff positioning or scan errors;
    c) rejecting or accepting said oscillometric profile based on presence or absence of the irregularities;
    d) when the oscillometric profile is accepted, determining preliminary threshold values for a systole and a diastole, said preferred values being 70% of the maximum amplitude of the profile for the systole and 50% of the maximum amplitude of the profile for the diastole;
    e) categorizing the profile into low, normal, or high blood pressure ranges based on said preliminary systole and diastole values;
    f) calculating a first offset for the systole depending on said categorization;

g) estimating a tissue coupling by assessing said maximum amplitude and a systolic slope of said profile in the low pressure range in order to calculate a second offset;
h) assessing the spectral content of the arterial pulse at different pressure steps of an oscillometric scan; and
i) assessing a diastolic slope of the oscillometric profile;
j) calculating final systolic and diastolic thresholds based on the diastolic slope and the systolic slope;
k) adding the first offset to the final systolic threshold and subtracting the second offset from the final systolic threshold and from the final diastolic threshold to produce said calibrated, absolute blood pressure value; and ix) displaying said calibrated, absolute blood pressure value.

* * * * *